US007951949B2

(12) United States Patent
Nantermet et al.

(10) Patent No.: US 7,951,949 B2
(45) Date of Patent: May 31, 2011

(54) MACROCYCLIC AMINOPYRIDYL BETA-SECRETASE INHIBITORS FOR THE TREATMENT OF ALZHEIMER'S DISEASE

(75) Inventors: Philippe G. Nantermet, Lansdale, PA (US); Hemaka A. Rajapakse, Wyncote, PA (US); Harold G. Selnick, Ambler, PA (US); Keith P. Moore, North Wales, PA (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 1024 days.

(21) Appl. No.: 11/791,465

(22) PCT Filed: Nov. 18, 2005

(86) PCT No.: PCT/US2005/042233
§ 371 (c)(1),
(2), (4) Date: May 23, 2007

(87) PCT Pub. No.: WO2006/057983
PCT Pub. Date: Jun. 1, 2006

(65) Prior Publication Data
US 2008/0015213 A1 Jan. 17, 2008

Related U.S. Application Data

(60) Provisional application No. 60/630,319, filed on Nov. 23, 2004.

(51) Int. Cl.
*C07D 519/06* (2006.01)
*A61K 31/4353* (2006.01)
(52) U.S. Cl. .............. 546/80; 546/81; 546/89; 514/291; 514/292; 514/293
(58) Field of Classification Search ............ 546/80, 546/81, 89; 514/291, 292, 293
See application file for complete search history.

(56) References Cited

U.S. PATENT DOCUMENTS

| 6,333,410 | B1 | 12/2001 | Chari et al. |
| 6,525,074 | B2 | 2/2003 | deSolms et al. |
| 7,109,217 | B2 | 9/2006 | Coburn et al. |
| 2006/0058278 | A1 | 3/2006 | Coburn et al. |
| 2006/0149092 | A1 | 7/2006 | Nantermet et al. |
| 2006/0161020 | A1 | 7/2006 | Coburn et al. |
| 2006/0293380 | A1 | 12/2006 | Nantermet et al. |
| 2007/0037784 | A1 | 2/2007 | Coburn et al. |

FOREIGN PATENT DOCUMENTS

| WO | 02100399 | 12/2002 |
| WO | WO 03/106405 | 12/2003 |
| WO | WO 2005/005374 | 1/2005 |
| WO | WO 2005/051914 | 6/2005 |
| WO | WO 2005/065195 | 7/2005 |
| WO | WO 2005/103020 | 11/2005 |
| WO | WO 2005/103043 | 11/2005 |
| WO | WO 2006/015621 | 2/2006 |
| WO | WO 2006/055434 | 5/2006 |

OTHER PUBLICATIONS

Supplementary Search Report for counterpart EPO Appln. No. 05849049, dated Oct. 17, 2009.
Coburn, et al., J Med Chem, 2004, 47:6117-6119.
Stachel, et al., J Med Chem, 2004, 47: 6447-6450.

*Primary Examiner* — Rita J Desai
(74) *Attorney, Agent, or Firm* — Keith D. MacMillan; Gerard M. Devlin

(57) ABSTRACT

The present invention is directed to macrocyclic aminopyridyl compounds represented by general formula (I), which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

12 Claims, No Drawings

MACROCYCLIC AMINOPYRIDYL BETA-SECRETASE INHIBITORS FOR THE TREATMENT OF ALZHEIMER'S DISEASE

CROSS REFERENCE TO RELATED APPLICATIONS

This application claims priority under 35 U.S.C. §119(e) of U.S. provisional application Ser. No. 60/630,319, filed Nov. 23, 2004.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to the field of compounds which are inhibitors of the activity of the β-secretase enzyme, and to the use of the compounds for the treatment of diseases in which the β-secretase enzyme is involved, such as Alzheimer's disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and SAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβprotein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of $APP_s$ production of Aβ, and accumulation of β amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to novel macrocyclic aminopyridyl compounds represented by general formula (I)

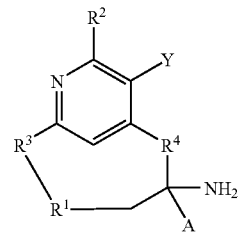

and pharmaceutically acceptable salts thereof, and individual enantiomers and diastereomers thereof, which are useful as inhibitors of the β-secretase enzyme.

The invention is also directed to pharmaceutical compositions which include an effective amount of a compound of formula (I), or pharmaceutically acceptable salts thereof, and individual enantiomers and diastereomers thereof, and a pharmaceutically acceptable carrier. The invention is also directed to methods of treating mammals for diseases in which the β-secretase enzyme is involved, such as Alzheimer's disease, and the use of the compounds and pharmaceutical compositions of the invention in the treatment of such diseases.

DETAILED DESCRIPTION OF THE INVENTION

The present invention is directed to compounds of formula (I):

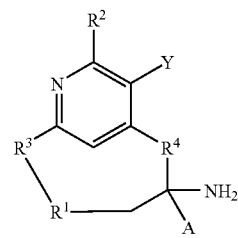

and pharmaceutically acceptable salts thereof, and individual enantiomers and diastereomers thereof, wherein:
Y is selected from the group consisting of
  (1) hydrogen,
  (2) —$C_{1-3}$ alkyl, wherein said alkyl is optionally substituted with one or more halogen,
  (3) halogen, and
  (4) cyano;
A is selected from the group consisting of
  (1) hydrogen,
  (2) —$C_{1-10}$ alkyl,
  (3) —$C_{2-10}$ alkenyl, and
  (4) —$C_{2-10}$ alkynyl
  wherein said alkyl, alkenyl or alkynyl is unsubstituted or substituted with one or more
    (a) halo,
    (b) —$C_{3-8}$ cycloalkyl,
    (c) —OH,
    (d) —CN,
    (e) —O—$C_{1-10}$ alkyl,
    (f) —$C_{6-10}$ aryl, or
    (g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl, and said aryl and heteroaryl groups are unsubstituted or substituted with one or more
(i) halo,
(ii) —OH,
(iii) —CN,
(iv) —O—$C_{1-10}$ alkyl,
(v) —$C_{1-10}$ alkyl,
(vi) —$C_{2-10}$ alkenyl,
(vii) —$C_{2-10}$ alkynyl, or
(viii) —$C_{3-8}$ cycloalkyl;

$R^1$ is selected from the group consisting of
(1) —$C_{6-10}$ arylene, or
(2) heteroarylene selected from the group consisting of divalent pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl, wherein said arylene or heteroarylene is unsubstituted or substituted with one or more
(a) halo,
(b) —$C_{1-10}$ alkyl,
(c) —$C_{2-10}$ alkenyl,
(d) —$C_{2-10}$ alkynyl,
(e) —OH,
(f) —CN,
(g) —O—$C_{1-10}$ alkyl, or
(h) —$C_{3-8}$ cycloalkyl;

$R^2$ is selected from the group consisting of:
(1) $(R^5—SO_2)N(R^6)$—, wherein $R^5$ is
(a) —$C_{1-10}$ alkyl,
(b) —$C_{2-10}$ alkenyl,
(c) —$C_{2-10}$ alkynyl,
(d) —$C_{3-8}$ cycloalkyl,
(e) —$C_{6-10}$ aryl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl, wherein said alkyl, alkenyl, alkynyl, cycloalkyl, aryl and heteroaryl is unsubstituted or substituted with one or more
(i) halo,
(ii) —OH,
(iii) —CN,
(iv) —O—$C_{1-10}$ alkyl,
(v) —$C_{1-10}$ alkyl,
(vi) —$C_{2-10}$ alkenyl,
(vii) —$C_{2-10}$ alkynyl,
(viii) —$C_{3-8}$ cycloalkyl,
(ix) —$C_{6-10}$ aryl, or
(x) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl, and said aryl and heteroaryl is unsubstituted or substituted with one or more
(A) halo,
(B) —OH,
(C) —CN,
(D) —O—$C_{1-10}$ alkyl,
(E) —$C_{3-8}$ cycloalkyl,
(F) —$C_{1-10}$ alkyl,
(G) —$C_{2-10}$ alkenyl, or
(H) —$C_{2-10}$ alkynyl;

$R^6$ is selected from the group consisting of
(a) hydrogen,
(b) —$C_{1-10}$ alkyl,
(c) —$C_{2-10}$ alkenyl,
(d) —$C_{2-10}$ alkynyl,
(e) —$C_{6-10}$ aryl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl, wherein said alkyl, alkenyl, alkynyl, aryl or heteroaryl. is unsubstituted or substituted with one or more
(i) halo,
(ii) —OH,
(iii) —CN,
(iv) —O—$C_{10}$ alkyl,
(v) —$C_{3-8}$ cycloalkyl,
(vi) —$C_{6-10}$ aryl, or
(vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl;

wherein said cycloalkyl, aryl or heteroaryl is unsubstituted or substituted with one or more
(A) halo,
(B) —OH,
(C) —CN,
(D) —O—$C_{1-10}$ alkyl,
(E) —$C_{3-8}$ cycloalkyl, or
(F) —$C_{6-10}$ aryl, or $R^5$ and $R^6$ may be linked to form a group —$CH_2(CH_2)_pCH_2$—, (2) —$C_{6-10}$ aryl, wherein said aryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) —$C_{1-10}$alkyl,
(vi) —$C_{6-10}$ aryl, (3)

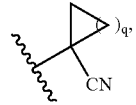

(4) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl, wherein said heteroaryl is unsubstituted or substituted with one or more
  (i) halo,
  (ii) —OH,
  (iii) —CN,
  (iv) —O—$C_{1-10}$ alkyl,
  (v) —$C_{3-8}$ cycloalkyl,
  (vi) —$C_{1-10}$ alkyl,
  (vii) —C(=O)—O—$C_{1-10}$ alkyl,
  (viii) —C(=O)—OH, and
  (ix) —C(=O)—$NR^cR^d$,
  (x) —$NR^cR^d$, wherein $R^c$ and $R^d$ are selected from the group consisting of
    (A) hydrogen, and
    (B) —$C_{1-10}$ alkyl,
(5) hydrogen, and
(6) —$CF_3$;

$R^3$ is

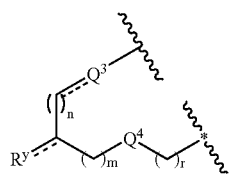

wherein if the dotted line leading to $Q^3$ is absent, then $Q^3$ is selected from the group consisting of
  (a) —$CH_2$—
  (b) —O—,
  (c) —$NR^x$—
  (d) —C(=O)—, and
  (e) —C(=O)—$NR^x$—,
  wherein $R^x$ is selected from the group consisting of
    (i) hydrogen,
    (ii) —$C_{1-10}$ alkyl,
    (iii) —$C_{2-10}$ alkenyl,
    (iv) —$C_{2-10}$ alkynyl,
    (v) —$C_{3-8}$ cycloalkyl,
    (vi) —$C_{0-6}$ alkylene-$C_{6-10}$ aryl,
    (vii) —$C_{0-6}$ alkylene-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl,
    (viii) —$C_{0-6}$ alkyl-$C_{3-8}$ cycloalkyl,
  and if the dotted line leading to $Q^3$ represents a bond, then $Q^3$ is —CH— or —$CH_2CH$—,
if the dotted line leading to $R^y$ is absent, then $R^y$ is selected from the group consisting of
(a) hydrogen,
(b) —$C_{1-10}$ alkyl,
(c) —$C_{2-10}$ alkenyl,
(d) —$C_{2-10}$ alkynyl,
(e) —$C_{3-8}$ cycloalkyl,
(f) —$C_{0-6}$ alkylene-$C_{6-10}$ aryl, or
(g) —$C_{0-6}$ alkylene-heteroaryl, wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl,
and if the dotted line leading to $R^y$ represents a bond, then $R^y$ is selected from the group consisting of
(a) =CH—$C_{1-10}$ alkyl,
(b) =CH—$C_{0-6}$ alkyl-$C_{6-10}$ aryl,
  wherein said alkyl, alkenyl, alkynyl, cycloalkyl, aryl or heteroaryl $R^y$ groups are unsubstituted or substituted with one or more
    (i) halo,
    (ii) —$C_{1-10}$ alkyl,
    (iii) —OH,
    (iv) —CN, or
    (v) —O—$C_{10}$ alkyl, or
    (vi) —$C_{3-8}$ cycloalkyl,
$Q^4$ is selected from the group consisting of
  (a) —$CH_2$—
  (b) —O—, and
  (c) —$NR^z$—
    wherein $R^z$ is selected from the group consisting of
      (i) hydrogen,
      (ii) —$C_{1-10}$ alkyl,
      (iii) —$C_{2-10}$ alkenyl,
      (iv) —$C_{2-10}$ alkynyl,
      (v) —$C_{3-8}$ cycloalkyl,
      (vi) —$C_{0-6}$ alkylene-$C_{6-10}$ aryl, or
      (vii) —$C_{0-6}$ alkylene-heteroaryl, wherein said heteroaryl is selected from the
      group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl,
$R^4$ is —$(CH_2)_s$-$Q^2$-$(CH_2)_t$, wherein $Q^2$ is selected from the group consisting of
  (1) —O—
  (2) —NH—,
  (3) —O—C(=O)—,
  (4) —C(=O)—O—,
  (5) —NHC(=O)—,
  (6) —C(=O)—NH—,
  (7) —CH=CH—,
  (8) —C(=O)—,
  (9) —$(CH_2)_u$—,
  (10)

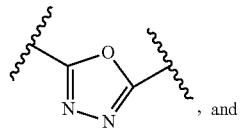, and (11)

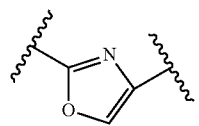

m is 0, 1 or 2;
n is 0, 1 or 2;
p is 1, 2 or 3;

q is 1, 2, 3, 4 or 5;
r is 0, 1 or 2;
s is 0 or 1;
t is 0 or 1; and
u is 0, 1 or 2.

In a preferred embodiment of the compounds of formula (I), Y is hydrogen.

In another preferred embodiment of the compounds of formula (I), $R^1$ is unsubstituted or substituted $—C_{6-10}$ arylene, preferably unsubstituted phenylene.

In another preferred embodiment of the compounds of formula (I), $R^4$ is $—(CH_2)_s-Q^2-(CH_2)_t$, wherein $Q^2$ is selected from the group consisting of
(1) —O—,
(2) —O—C(=O)—,
(3)

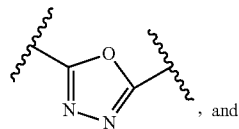, and (4)

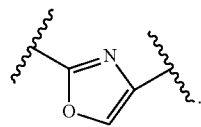.

When $Q^2$ is selected from —O—, —NH—, or —C(=O)—, then s and t are each preferably 1. When $Q^2$ is selected from —O—C(=O)— or —NHC(=O)—, then s is preferably 0 and t is preferably 1. When $Q^2$ is selected from —C(=O)—O— or —(C=O)—NH—, then s is preferably 1 and t is preferably 0. When $Q^2$ is —CH=CH, then preferably s is 0 and t is 1, or s is 1 and t is 0. When $Q^2$ is selected from the group consisting of

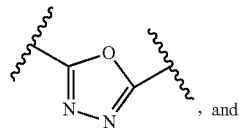, and

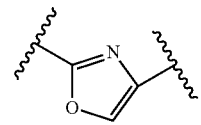

then s and t are preferably 0.

In preferred embodiments of the compounds of formula (I), A is selected from the group consisting of
(1) hydrogen, and
(2) $—C_{1-10}$ alkyl,
wherein said alkyl is unsubstituted or substituted with one or more
(a) halo,
(b) $—C_{3-8}$ cycloalkyl,
(c) —CN
(d) $—O—C_{1-10}$ alkyl,
(e) phenyl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, indynyl and benzoxazolyl.

In a more preferred embodiment of the compounds of the formula (I), A is $—C_{1-10}$ alkyl (preferably methyl), wherein said alkyl is unsubstituted or substituted with one or more halo (preferably fluoro).

In a preferred embodiment of the compounds of formula (I), $R^2$ is selected from the group consisting of $(R^5—SO_2)N(R^6)—$, wherein $R^5$ is $—C_{1-6}$ alkyl, wherein said alkyl is unsubstituted or substituted with one or more
(i) halo,
(ii) —OH,
(iii) —CN,
(iv) $—O—C_{1-6}$ alkyl, or
(v) $—C_{1-6}$ alkyl, $R^6$ is selected from the group consisting of
(a) hydrogen,
(b) $—C_{1-6}$ alkyl, or
(c) $—C_{6-10}$ aryl,
wherein said alkyl and aryl is unsubstituted or substituted with one or more
(i) halo,
(ii) —OH,
(iii) —CN,
(iv) $—O—C_{1-6}$ alkyl,
(v) $—C_{1-6}$ alkyl, or $R^5$ and $R^6$ are linked to form a group $—CH_2(CH_2)_pCH_2—$.

Another preferred $R^2$ group is $—C_{6-10}$ aryl, unsubstituted or substituted as described above. Preferred aryl groups are phenyl groups, unsubstituted or substituted with cyano. A preferred $R^2$ substituent is shown below:

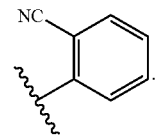

Another preferred $R^2$ substituent is

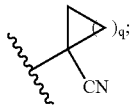

wherein q is 1, 2 or 3.

Another preferred $R^2$ substituent is heteroaryl, either unsubstituted or substituted as described above. A preferred heteroaryl group is furanyl or oxazolyl, either unsubstituted or substituted as described above. A preferred furanyl or oxazolyl substituent is depicted below:

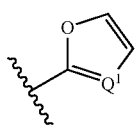

wherein $Q^1$ is selected from the group consisting of
(a) N, and
(b) C—$R^b$, wherein $R^b$ is selected from the group consisting of
   (i) —CN, and
   (ii) —C(=O)—O—$C_{1-10}$ alkyl,
   (iii) —C(=O)—OH, and
   (iv) —C(=O)—$NR^cR^d$,
   (v) —$NR^cR^d$, wherein $R^c$ and $R^d$ are selected from the group consisting of
      (A) hydrogen, and
      (B) —$C_{1-10}$ alkyl.

In one embodiment of the compounds of formula (I) when the dotted line leading to $Q^3$ is absent and $Q^3$ is $NR^x$, $R^x$ is preferably hydrogen, and n is preferably 1.

In an alternative embodiment of the compounds of formula (I) when the dotted line leading to $Q^3$ is absent, $Q^3$ is —O— and n is preferably 1.

In another embodiment when the dotted line leading to $Q^3$ is —C(=O)—$NR^x$, $R^x$ is preferably hydrogen, and n is preferably 1.

In certain embodiments, the dotted line leading to $R^y$ is absent and $R^y$ is selected from the group consisting of
(a) hydrogen,
(b) —$C_{1-10}$ alkyl, or
(c) —$C_{0-6}$ alkyl-$C_{6-10}$ aryl, wherein said alkyl or aryl or unsusbsituted or substituted with one or more halo (preferably fluoro).

In preferred embodiments, $Q^4$ is $CH_2$, m is preferably 1 and r is preferably 0.

In another embodiment, the invention is directed to compounds of Formula (II):

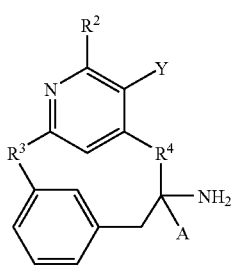

(II)

and pharmaceutically acceptable salts thereof, and individual enantiomers and diastereomers thereof, wherein A, Y, $R^2$, $R^3$ and $R^4$ are as defined above.

Another embodiment of the present invention includes a compound which is selected from the title compounds of the following Examples and pharmaceutically acceptable salts thereof.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkylene," by itself or as part of another substituent, means a saturated straight or branched chain divalent hydrocarbon radical having the number of carbon atoms designated. The term $C_0$ alkylene (for example, in the radical "—$C_0$alkylene-$C_{6-10}$ aryl") means that the alkylene group is absent.

As used herein, the term "cycloalkyl," by itself or as part of another substituent, means a saturated cyclic hydrocarbon radical having the number of carbon atoms designated (e.g., $C_{3-8}$ cycloalkyl means a cycloalkyl group having from three to eight carbon atoms). Exemplary cycloalkyl groups include cyclopropyl, cyclobutyl, cyclopentyl, cyclohexyl and the like.

As used herein, the term "alkenyl," by itself of as part of another substituent, means a straight or branched chain hydrocarbon radical having a single carbon-carbon double bond and having the number of carbon atoms designated (e.g., $C_{2-10}$ alkenyl means an alkenyl group having from one to ten carbon atoms). Preferred alkenyl groups for use in the invention are $C_{2-6}$ alkenyl groups, having from two to six carbon atoms. Exemplary alkenyl groups include ethenyl, n-propenyl, isopropenyl, butenyl, and the like.

As used herein, the term "alkynyl", by itself or as part of another substituent, means a saturated straight or branched chain hydrocarbon radical having the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems as well as single ring systems. Preferred aryl groups for use in the invention include phenyl and naphthyl.

As used herein, the term "arylene," by itself or as part of another substituent, means a divalent aromatic or cyclic radical. having the number of carbon atoms designated (e.g., $C_{6-10}$ arylene means an arylene group having from six to ten carbons atoms). The term "arylene" includes multiple ring systems as well as single ring systems. Preferred arylene groups for use in the invention include phenylene and naphthylene.

As used herein, the term "heteroaryl," by itself or as part of another substituent, means an aromatic cyclic radical having at least one ring heteroatom (O, N or S). The term "heteroaryl" includes multiple ring systems as well as single ring systems. Exemplary heteroaryl groups for use in the invention include furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, benzimidazolyl, quinolinyl, isoquinolinyl, tetrazolyl, indazolyl, napthyridinyl, triazolyl, oxazolyl, oxadiazolyl, thiazolyl, thiadiazolyl, isoxazolyl, tetrahydroquinolinyl, tetrahydroisoquinolinyl, indynyl and dihydroindolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "heteroarylene," by itself or as part of another substituent, means an aromatic cyclic divalent radical having at least one ring heteroatom (O, N or S).

The term "halo" or "halogen" includes fluoro, chloro, bromo and iodo.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The compounds of the present invention are prepared by the methods outlined in Schemes 1.1 to 5.8, below, and the intermediates and examples herein.

The compounds of the present invention are prepared by the methods outlined in Schemes 1.1-5.8, illustrated below.

Scheme 1.1, describes the preparation of derivatives of type 1.1a, as well as the corresponding triflate analogs 1.1b and 1.1c. Starting from glycine Schiff base, more elaborated bromides of type 1.1d and 1.1e were prepared.

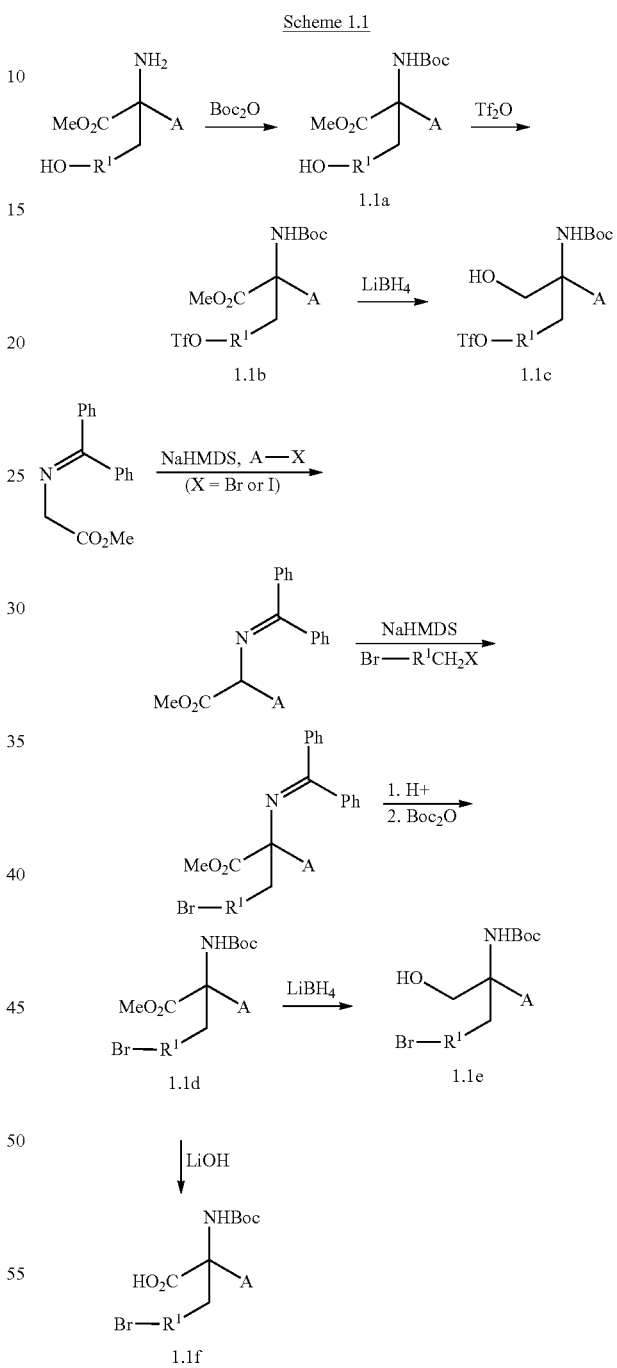

Scheme 2.1 describes a sequence leading to 2,6-dichloro pyridine derivatives from 2,6-dichoroisonicotinate. Methyl ester hydrolysis gives acid 2.1a, which was transformed via a two step sequence to acylhydrazide 2.1b. Benzyl alcohol 2.1c is readily accessed via ester reduction, and was transformed to the corresponding benzyl bromide with $CBr_4/Ph_3P$.

Scheme 2.1

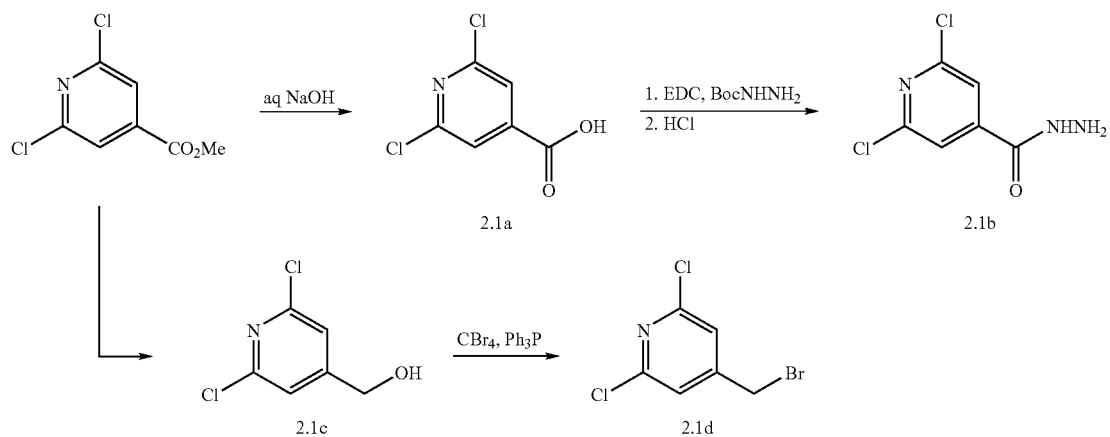

Sulfonylation of 2,6-dichloroisinicotinate gave key intermediate 2.2a, which was then be transformed to acid 2.2b or alcohol 2.2c as described above. Acylhydrazide 2.2d was derived from acid 2.2b while alcohol 2.2c was further advanced to bromide 2.2e. Alternatively, siliyl protection of alcohol 2.2c affords silyl ether 2.2f.

Homo-allylic amies of type 3.1b were prepared via conjugate addition of phthalimide to α,β-unsaturated aldehydes, followed by Wittig homologation to give compounds of type 3.1a, as described in Scheme 3.1 (See Bergman, E. D., Migron, Y. *Organic Preparations and Procedures Int.* 1976, 8, 75-80). Pthalimide deprotection with hydrazine gives pri-

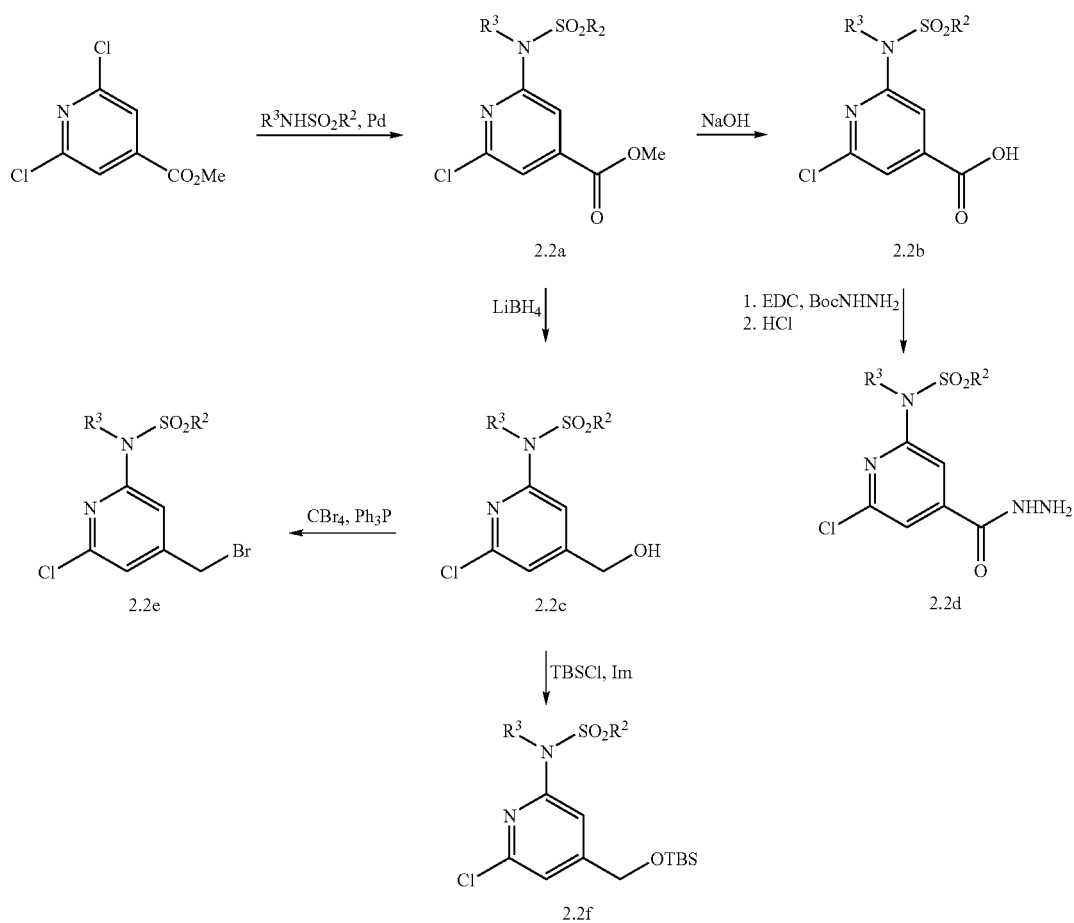

mary amine 3.1b, which were Boc protected without further functionalization to afford 3.1c. Alternatively, 3.1b underwent a reductive amination followed by Boc protection to give amines of type 3.1d. Boc protected amine 3.1c can also be alkylated under basic conditions to afford 3.1d.

Conjugate addition of vinylmagnesium bromide anion to 3.3a, followed by nitro reduction and Boc protection as described in Scheme 3.3 affords another route to 3.1b. As described in Scheme 3.1, this route also enables further substitution of the Boc protected primary amine.

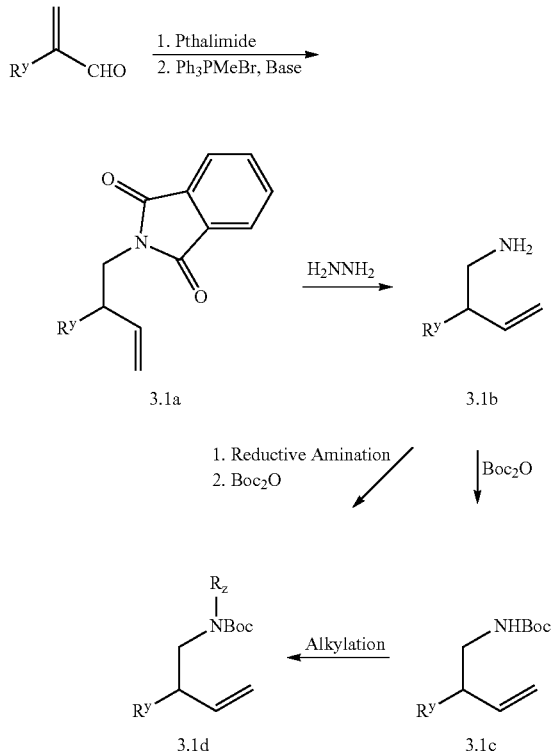

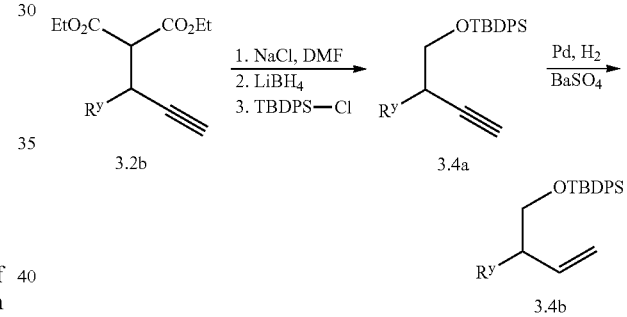

Scheme 3.4 shows the synthesis of alcohols 3.4a and 3.4b from intermediate 3.2b. Decarboxylation of 3.2b using conditions described by Krapcho, ester reduction and alcohol protection affords 3.4a. Lindlar reduction of the alkyne gives homoallylic alcohol 3.4b.

Scheme 3.2 describes an alternate synthesis of amines of type 3.1c and 3.1d. Condensation of diethylmalonate with an aldehyde provides the requisite α,β-unsaturated system 3.2a. Conjugate addition of TMS acetylene Grignard reagent, followed by desilylation affords 3.2b. Ester hydrolysis under basic conditions, followed by Curtius rearrangement affords homo propargylamine 3.2c. Lindlar reduction gives access to 3.1c, which was further alkylated to give 3.1d.

As shown in Scheme 3.5, glutaric acid derivatives of type 3.5a were monoesterified. Acid reduction, followed by iodination fo the newly generated alcohol afforded iodides of type 3.5b.

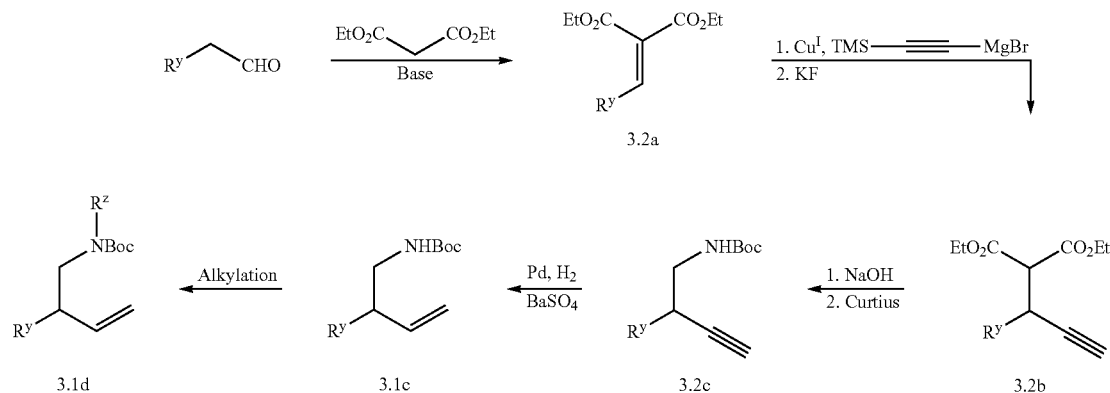

Scheme 3.5

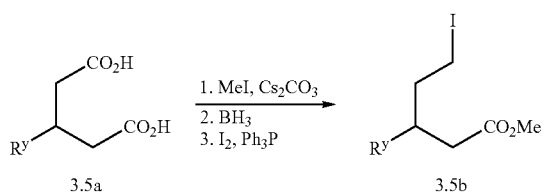

Coupling of intermediates 1.1b and 1.1d with terminal olefin 4.1a (For synthesis, see: Boeckman, R. K., Jr.; Charette, A. B.; Asberom, T.; Johnston, B. H. *J. Am. Chem. Soc.*, 1991, 113, 5337-53) can be accomplished using Suzuki conditions to give adduct 4.1b. Ester reduction with LiBH$_4$ gives alcohol 4.1d, while saponification affords acid 4.1e.

Scheme 4.1

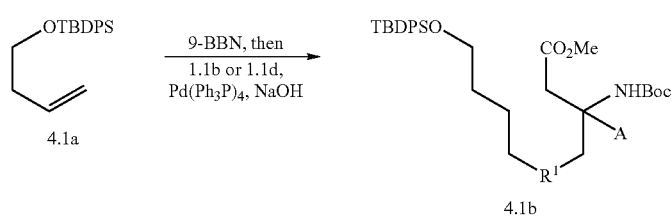

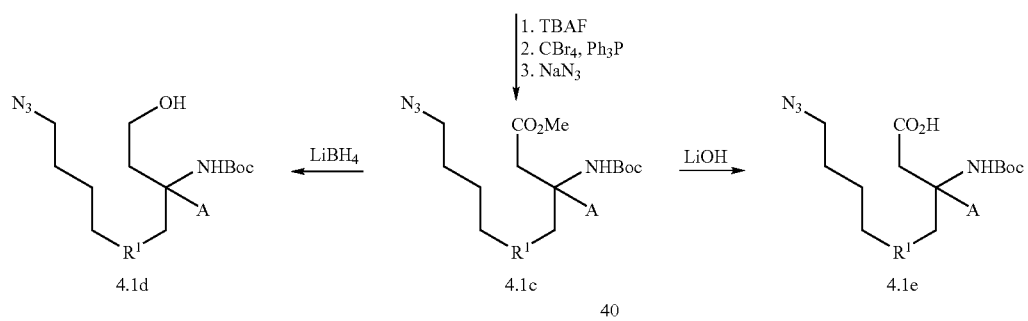

Intermediates of type 4.2b and 4.2c can be synthesized using a protocol similar to that described above, as shown in Scheme 4.2. This route can be utilized with either a primary or secondary Boc protected amine.

Scheme 4.2

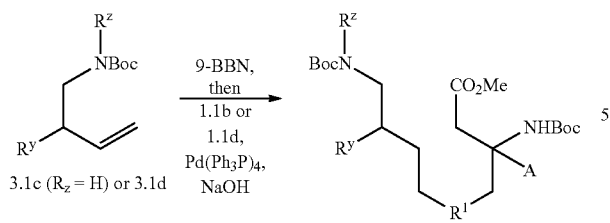

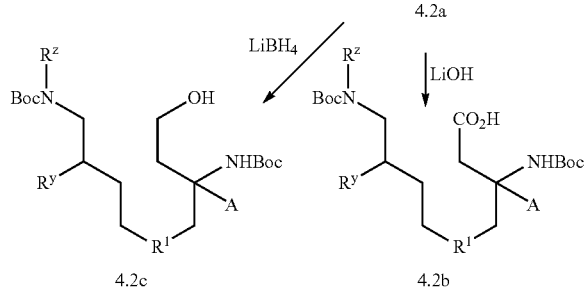

Olefins of type 4.3c were accessed via two methods, as described in Scheme 4.3. Suzuki coupling of olefin 3.2f with 1.1b or 1.1d, followed by oxidation and Wittig homologation gives the desired intermediate. Alternatively, hydroboration of excess 1,5 diene 4.3b, followed by Suzuki coupling enables direct access of 4.3c. Ester hydrolysis gives acid 4.3d, and reduction yields alcohol 4.3e.

Scheme 4.3

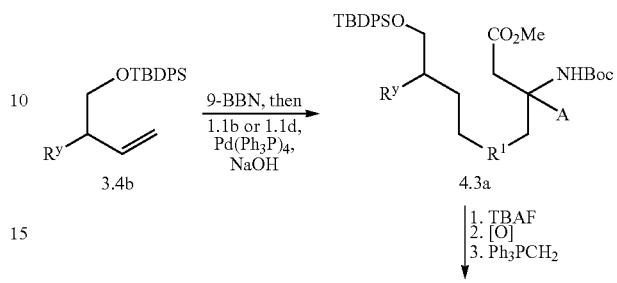

-continued

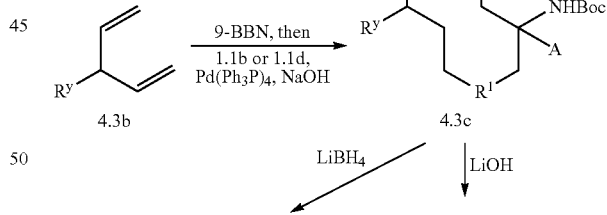

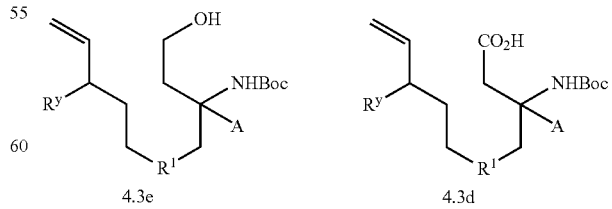

As shown in Scheme 4.4 intermediates of type 4.4a and 4.4b was accessed using a procedure similar to that described in Scheme 4.2.

Scheme 4.4

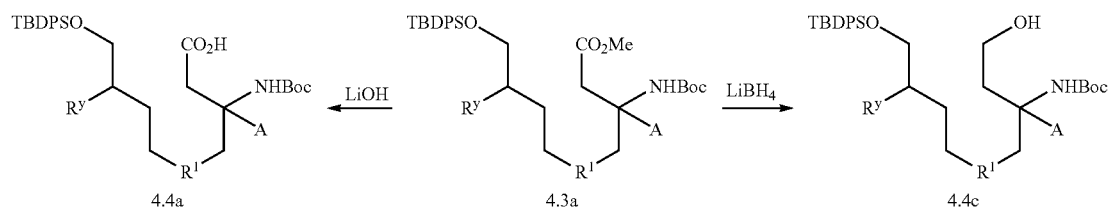

Etherification of benzylic bromides 2.1d or 2.2c with alcohol 4.1d was accomplished with silver trifluoromethanesulfonate. The azide functionality of adduct 5.1a was reduced under Staudinger conditions. Macroamination yields primary aminopyridine 5.1b. Reductive amination or mono alkylation of the primary amine prior to ring closure gave macroether adducts of type 5.1c. When benzyl bromide 2.1d is used for this sequence, further elaboration of the macrocyclic chloro-aminopyridines 5.1b and 5.2c is possible utilizing standard Negishi coupling conditions. Deprotection of the Boc group affords adducts-5.1d and 5.1e.

Scheme 5.1

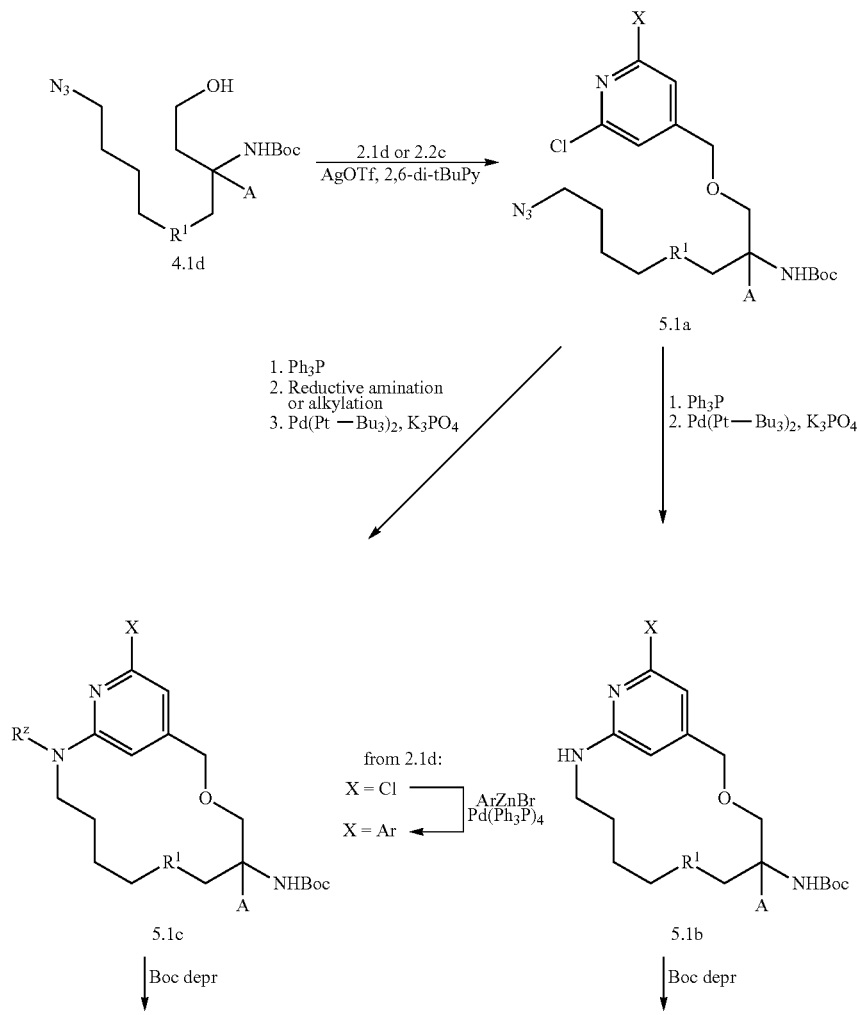

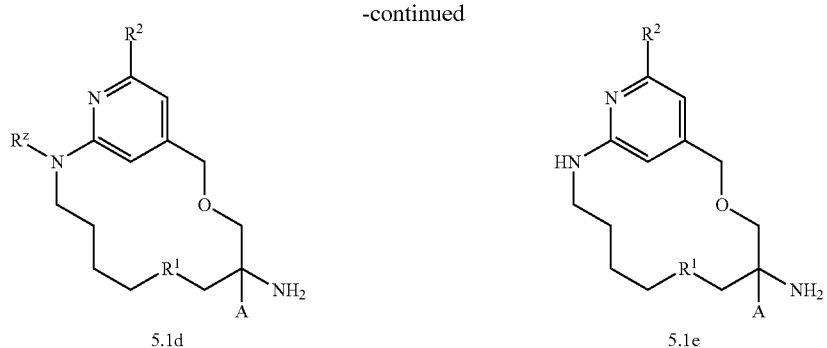
The synthesis of macrolactones such as 5.2d and 5.2e is depicted in Scheme 5.2, utilizing a similar strategy as described for Scheme 5.1. The central coupling reaction is performed using $CsCO_3$ base.
Scheme 5.2
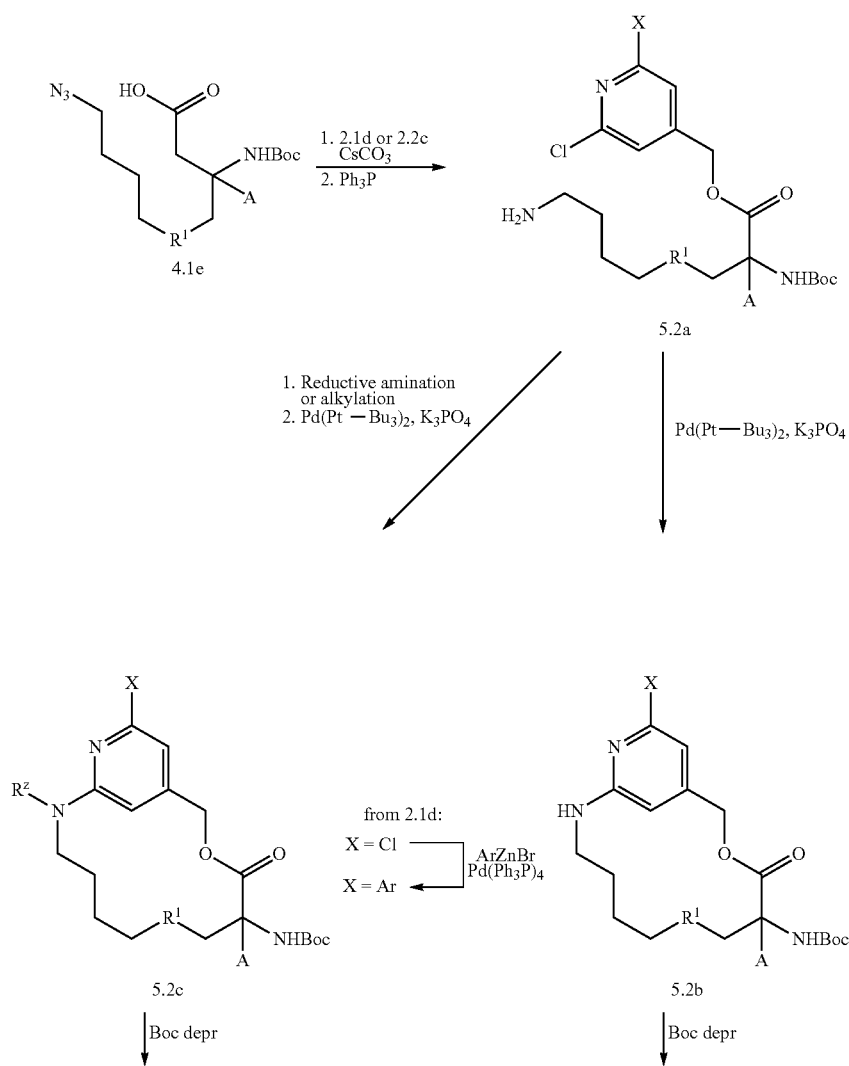

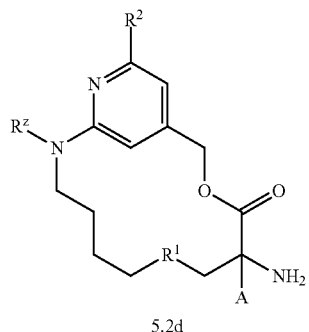

5.2d

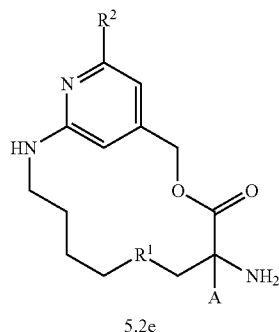

5.2e

Syntheses of macroethers of type 5.3b and 5.3c, and macroesters of type 5.4b and 5.4b and 5.4c are depicted in Schemes 5.3 and 5.4 respectively. The strategy utilized is very similar to that discussed in Scheme 5.1, where ring closure is accomplished through a macroamination strategy. When benzyl bromide 2.1d is utilized in the first step of these Schemes, the resulting 2-chloroaminopyridine functionality of 5.3b and 5.4b can be further functionalized after tertiarycarbinamine protection. Aryl coupling under Negishi conditions, followed by Boc deprotection affords compounds of type 5.3c and 5.4c.

Scheme 5.3

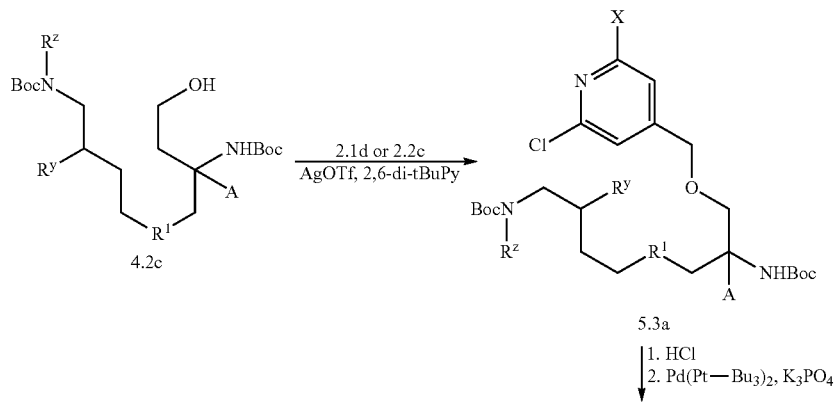

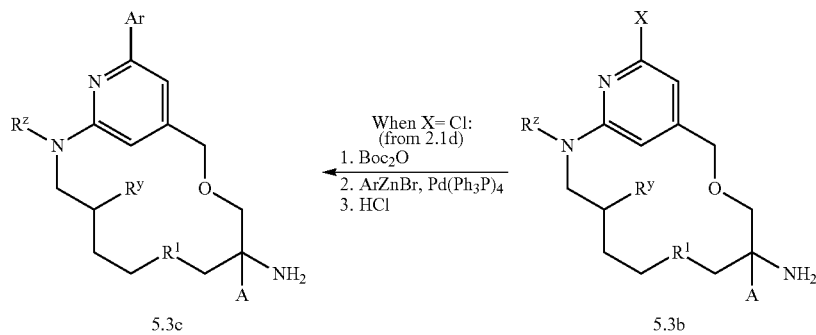

Scheme 5.4
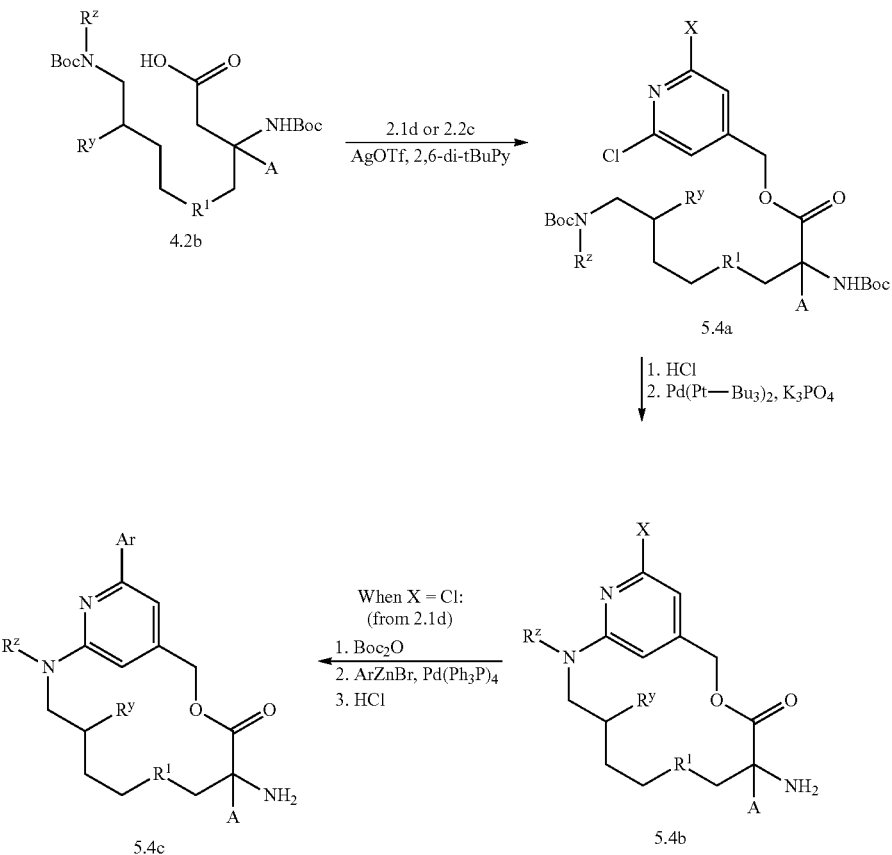
Described in Scheme 5.5 is the synthesis of macrocycles of type 5.5b and 5.5c, using a strategy similar to that of Scheme 5.1. The ring closure is accomplished through an intramolecular Heck reaction.
Scheme 5.5
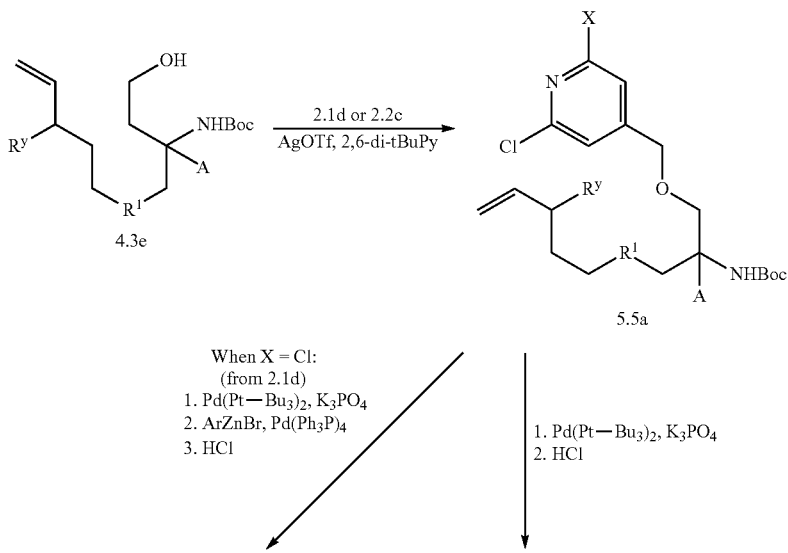

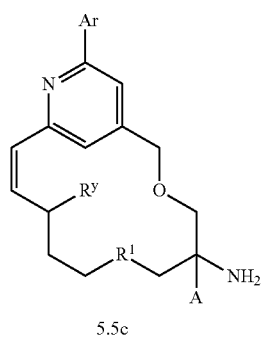

5.5c

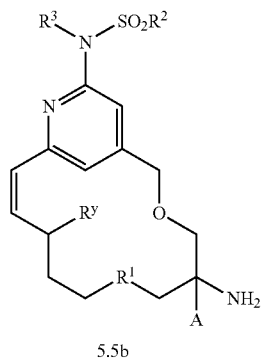

5.5b

Described in Scheme 5.6 is the synthesis of macrocycles of type 5.6b and 5.6c, using a strategy similar to that of Scheme 5.1. The ring closure is accomplished through an intramolecular Heck reaction.

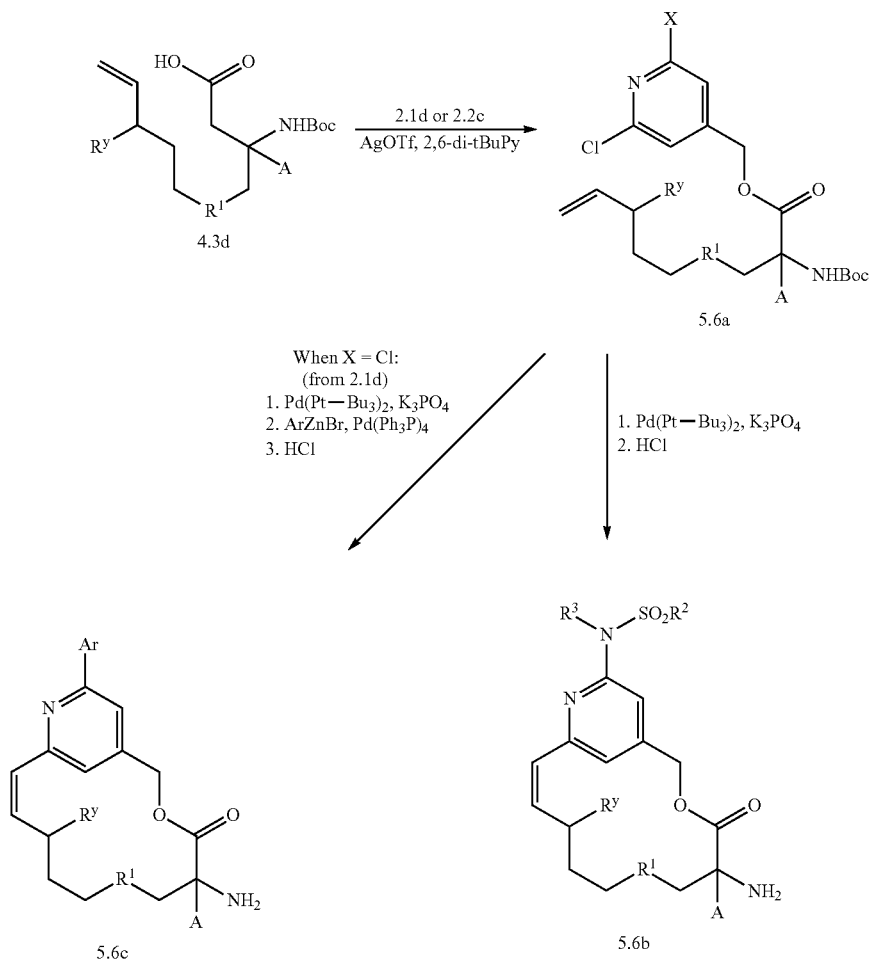

Described in Scheme 5.7 is the synthesis of macrocycles of type 5.7b and 5.7c, using a strategy similar to that of Scheme 5.1. The ring closure is accomplished through a palladium catalyzed intramolecular etherification reaction (for conditions, see: Kataoka, N.; Shelby, Q.; Stambuli, J. P.; Hartwig, J. F. *J. Org. Chem.* 2002, 67, 5553-5566).

Scheme 5.7
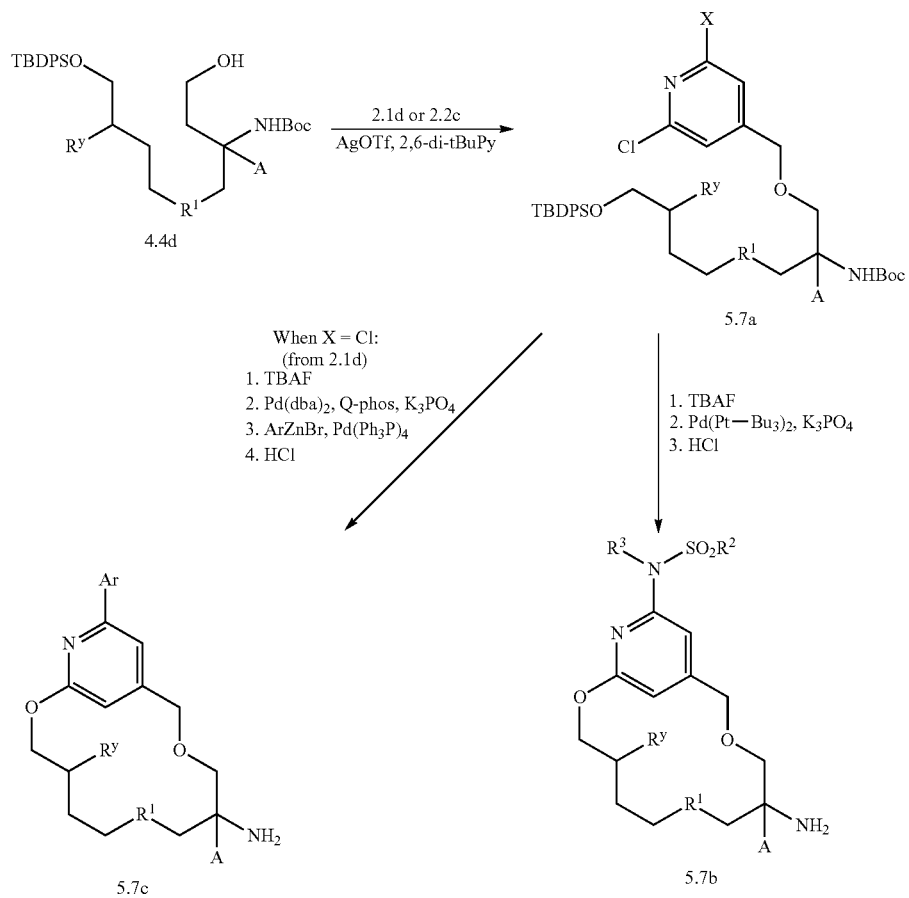
Described in Scheme 5.8 is the synthesis of macrocycles of type 5.8b and 5.8c, using a strategy similar to that of Scheme 5.1. The ring closure is accomplished through a palladium catalyzed intramolecular etherification reaction (for conditions, see: Kataoka, N.; Shelby, Q.; Stambuli, J. P.; Hartwig, J. F. *J. Org. Chem.* 2002, 67, 5553-5566).
Scheme 5.8
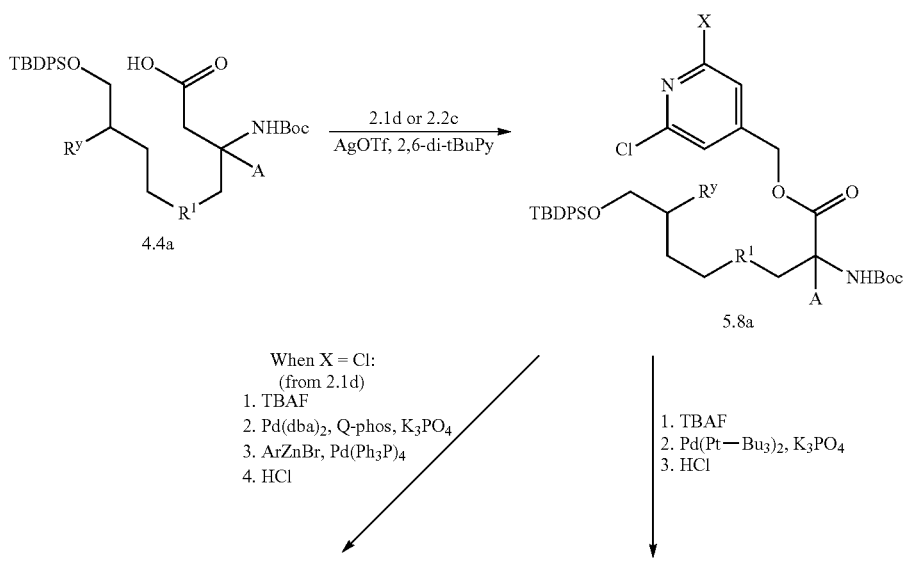

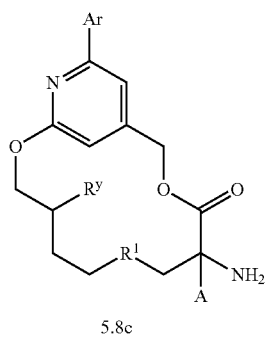

5.8c

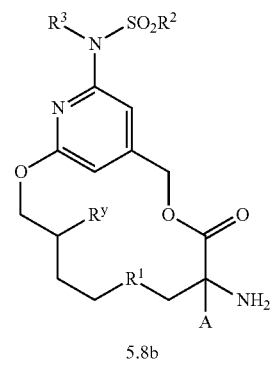

5.8b

As shown in Scheme 5.9, starting with iodides of type 3.5b, formation of the corresponding zincate with activated zinc, followed by coupling with aryl chloride 2.2f affords 5.9a. Ester reduction, transformation of the resulting alcohol to the corresponding iodide and a second Negishi coupling affords intermediate 5.9c. Silyl ether removal, ester hydrolysis and macrolactonization completes the synthesis of molecules of type 5.9d.

Scheme 5.9

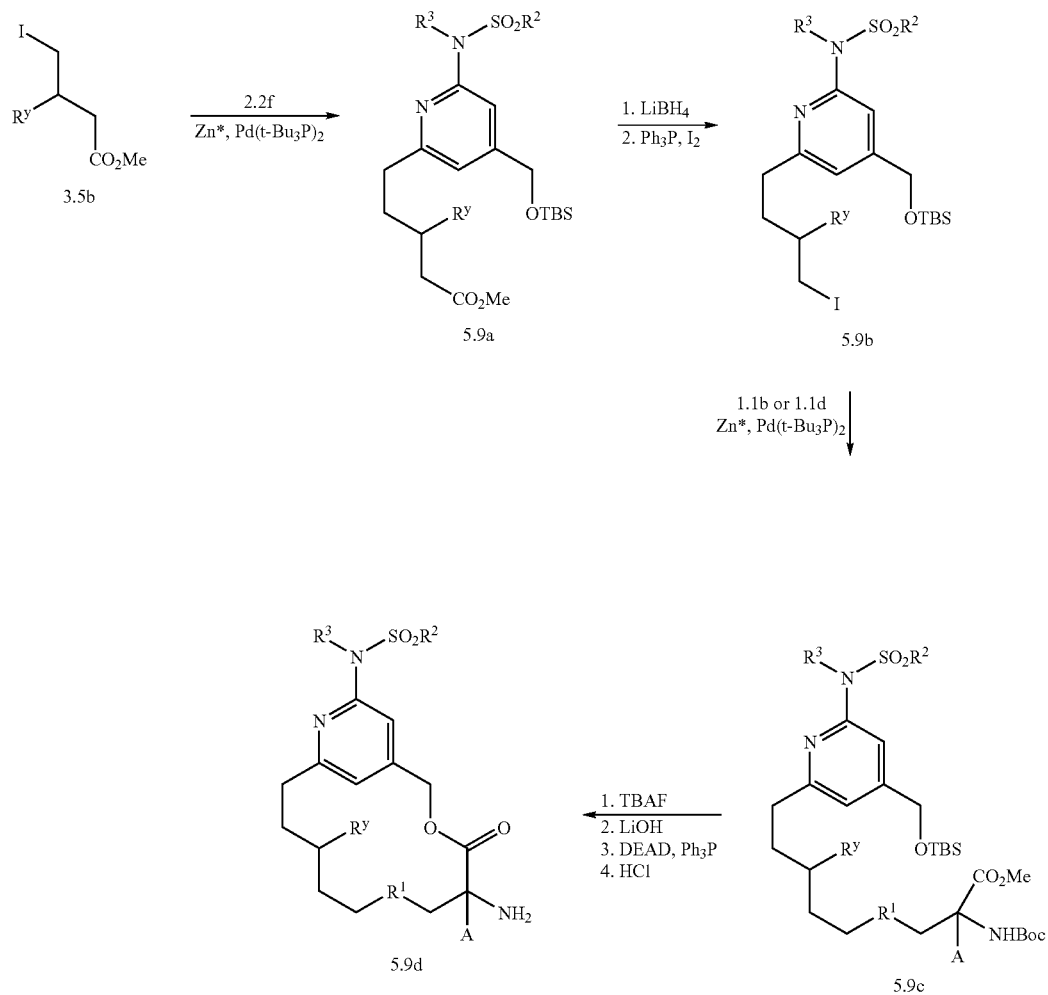

As depicted in Scheme 5.10, 5.9c can be synthesized utilizing an alternate route. Starting with 1,5-pentadiene 3.5b, monohydroboration followed by Suzuki coupling affords 5.10a. A second Suzuki coupling with 2.2f affords 5.9c through an alternate route.

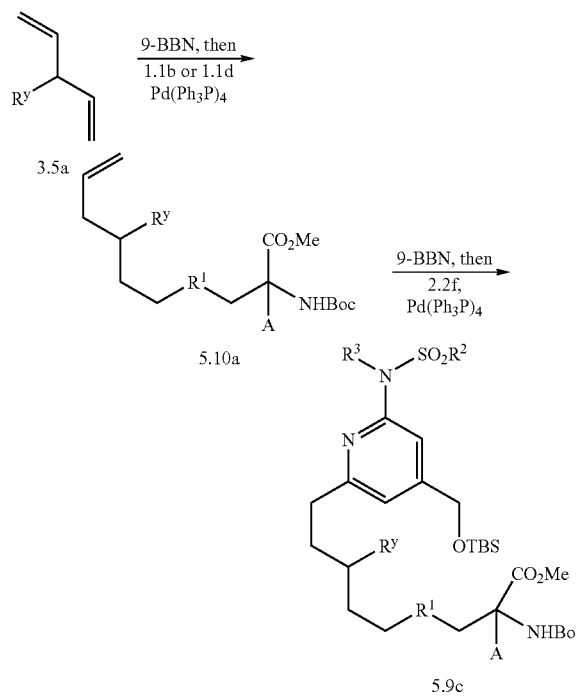

Described in Scheme 5.11 is the synthesis of macrocycles of type 5.11d and 5.11e. Acid 1.1f is alkylated with benzyl bromide derivative 2.2e to afford adduct 5.11a. Bis allylation then gives 5.11b, which can undergo a ring closing metathesis reaction to afford 5.11c. Boc deprotection gives 5.11d. Reduction of the olefin, then Boc deprotection affords 5.11e.

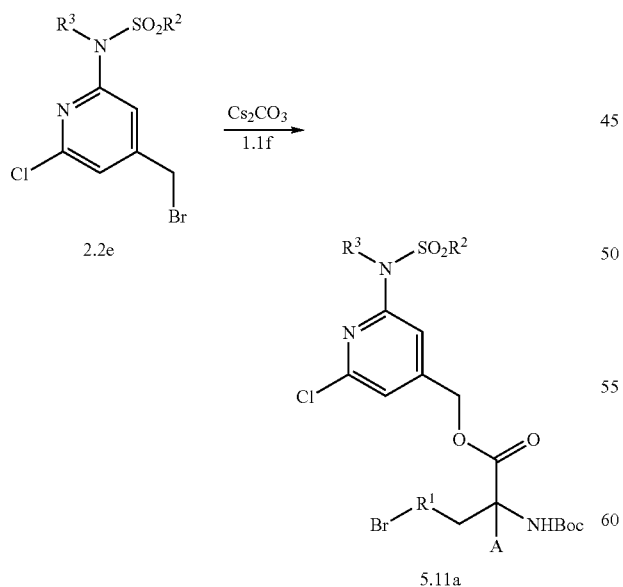

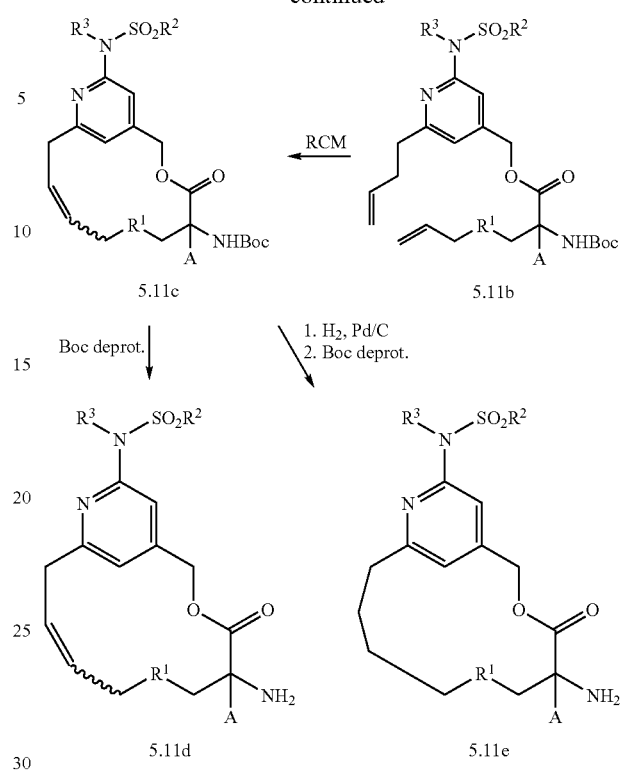

Compounds of type 5.2d or 5.2e can be selectively chorinated on the central pyridyl ring to give compounds of type 5.12a, as described in Scheme 5.12.

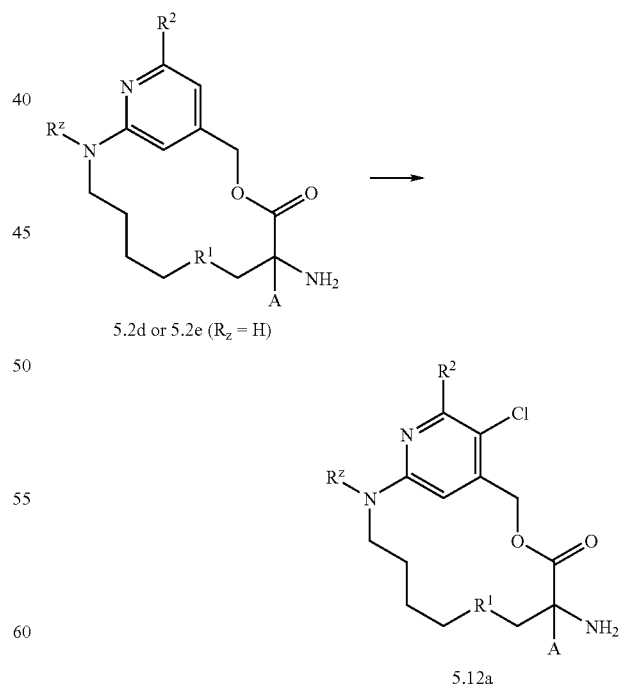

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors or gamma-secretase inhibitors; tau phosphorylation inhibitors; M1 receptor positive allosteric modulators; blockers of Aβ oligomer formation; 5-HT modulators, such as PRX-03140, GSK 742467, SGS-518, FK-962, SL-65.0155, SRA-333 and xaliproden; p25/CDK5 inhibitors; NK1/NK3 receptor antagonists; COX-2 inhibitors; HMG-CoA reductase inhibitors; NSAIDs including ibuprofen; vitamin E; anti-amyloid antibodies, including anti-amyloid humanized monoclonal antibodies; anti-inflammatory compounds such as (R)-flurbiprofen, nitroflurbiprofen, rosiglitazone, ND-1251, VP-025, HT-0712 and EHT-202; CB-1 receptor antagonists or CB-1 receptor inverse agonists; antibiotics such as doxycycline and rifampin; N-methyl-D-aspartate (NMDA) receptor antagonists, such as memantine and neramexane; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ antagonists such as ABT-834, ABT 829 and GSK 189254; AMPA agonists or AMPA modulators, such as CX-717, LY 451395 and S-18986; PDE IV inhibitors; $GABA_A$ inverse agonists; neuronal nicotinic agonists; selective M1 agonists; microtobubule affinity regulating kinase (MARK) ligands; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating Alzheimer's disease or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

FRET Assay: A homogeneous end point fluorescence resonance energy transfer (FRET) assay is employed with the substrate ([TAMRA-5-CO-EEISEVNLDAEF-NHQSY] QFRET), which is cleaved by BACE 1 to release the fluorescence from TAMRA. The Km of the substrate is not determined due to the limit of solubility of the substrate. A typical reaction contains approximately 30 nM enzyme, 1.25 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency of compounds, solutions of inhibitor in DMSO (four concentrations of the inhibitors are prepared: 1 mM, 100 µM, 10 µM, 1 µM) are included in the reactions mixture (final DMSO concentration is 0.8%). All experiments are conducted at rt using the standard reaction conditions described above. To determine the $IC_{50}$ of the compound, competitive equation $V0/Vi=1+[I]/[IC50]$ is used to predict the inhibitory potency of the compounds. The errors in reproducing the dissociation constants are typically less than two-fold.

HPLC assay: A homogeneous end point HPLC assay is used with the substrate (coumarin-CO-REVNFEVEFR), which is cleaved by BACE 1 to release the N-terminal fragment attached with coumarin. The Km of the substrate is greater than 100 µM and can not be determined due to the limit of solubility of the substrate. A typical reaction contains approximately 2 nM enzyme, 1.0 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and is stopped by the addition of 25 µL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared and the concentration rage is dependent on the potency predicted by FRET) are included in the reaction mixture (final DMSO concentration is 10%). All experiments are conducted at rt using the standard reaction conditions described above. To determine the $IC_{50}$ of the compound, four parameters equation is used for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 100 µM. Such a result is indicative of the intrinsic activity of the compounds in use as inhibitors of the beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

The following abbreviations are used throughout the text:
Me: methyl
Et: ethyl
Bu: butyl
t-Bu: tert-butyl
Ar: aryl
Ph: phenyl
Ac: acetyl
Bn: benzyl
Py: pyridine
Boc: tert-butyloxy carbonyl
TFA: trifluoroacetic acid
DCM: dichloromethane
DMA: dimthylacetamide
DMF: N,N'-dimethyl formamide
TBAF: tetra-n-butylaminonium fluoride
HMDS: hexamethyldisilazane
THF: tetrahydrofuran
DMSO: dimethylsulfoxide
EDTA: ethylene diamine tetraacetic acid
TMS: trimethylsilyl
9-BBN: 9-borabicyclo[3.3.1]nonane
EDC: 1-Ethyl-3-(3-dimethylaminopropyl)-carbodiimide
BSA: bovine serum albumin
CHAPS: 3-[(3-cholamidopropyl)dimethylammonio]-2-hydroxy-1-propanesulfonate
rt: room temperature
h: hours
aq: aqueous
HPLC: high performance liquid chromatography Intermediate I.1.a.1 (Scheme 1.1)

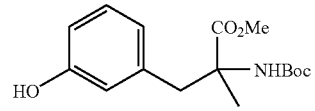

To a suspension of alphamethyl m-tyrosine methyl ester hydrochloride monohydrate (10.4 g, 39.4 mmol) in THF (300 mL) was added diisopropylethyl amine (7.6 mL, 43.4 mmol) and ditertbutyldicarbonate (9.1 g, 41.4 mmol) and the reaction mixture was stirred at RT for 24 h. The reaction mixture was concentrated in vacuo to ½ volume, diluted with EtOAc and diethyl ether, washed with 10% aq $KHSO_4$, and then alternatively with water and brine until aq pH=7, dried over $Na_2SO_4$, concentrated in vacuo, and purified by flash chromatography (300 g silica, 0-60% EtOAc in hexanes) to provide intermediate I.1.a.1. $^1H$ NMR (400 MHz, $CDCl_3$) δ 7.12 (app. t, J=8 Hz, 1H), 6.72 (dd, J=8, 2.4 Hz, 1H), 6.63 (d, J=8 Hz, 1H), 6.58 (dd, J=2.5, 2.4 Hz, 1H), 5.35 (br s, 1H), 5.16 (br s, 1H), 3.75 (s, 3H), 3.28 (m, 1H), 3.15 (B of AB, d, J=13.3 Hz, 1H), 1.55 (br s, 3H), 1.47 (s, 9H).

Intermediate I.1.b.1 (Scheme 1.1)

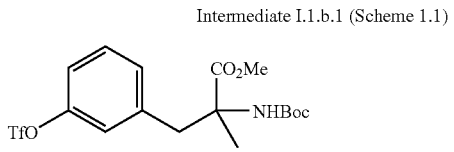

To a solution of intermediate I.1.a.1 (6.62 g, 21.4 mmol) in DCM (50 mL) cooled to 0° C. was added 2,6-lutidine (2.9 mL, 24.6 mmol) and triflic anhydride (4 mL, 23.5 mmol) dropwise. The reaction mixture was stirred at 0° C. for 10 min, diluted with water, extracted with DCM twice. The combined organic fraction was dried over $Na_2SO_4$, concentrated in vacuo, and purified by flash chromatography (300 g silica, 0-30% EtOAc in hexanes) to provide intermediate I.1.b.1. $^1$H NMR (400 MHz, $CDCl_3$) δ 7.35 (app. t, J=8 Hz, 1H), 7.15 (dd, J=8, 2.4 Hz, 1H), 7.11 (d, J=8 Hz, 1H), 7.0 (dd, J=2.5, 2.4 Hz, 1H), 5.19 (br s, 1H), 3.77 (s, 3H), 3.52 (A of AB, br d, J=13.6 Hz, 1H), 3.27 (B of AB, d, J=13.6 Hz, 1H), 1.56 (s, 3H), 1.48 (s, 9H).

Intermediate I.1.c.1 (Scheme 1.1)

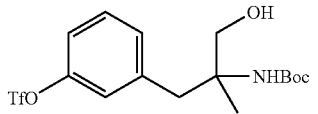

To a solution of intermediate I.1.b.1 (1.00 g, 2.27 mmol) in 20 mL anhydrous tetrahydrofuran cooled to 0° C. under an atmosphere of argon was added lithium borohydride (0.236 mL, 0.473 mmol, 2.0M solution in THF). After warming to room temperature over 2 hr., the reaction was cooled back down to 0° C. and quenched with MeOH. It was diluted with water (50 mL) and extracted with EtOAc (2×50 mL). The organic layers were combined, washed with brine (2×50 mL), dried over sodium sulfate, and concentrated in vacuo. Purification by flash chromatography (90 g silica, 0-45% EtOAc in hexanes) gave intermediate I.1.c.1 as a white solid. $^1$H NMR (400 MHz, $CDCl_3$) δ 7.38 (app t, J=7.9 Hz, 1H), 7.23 (d, J=7.9 Hz, 1H), 7.18-7.15 (m, 1H), 7.12 (s, 1H), 4.46 (s, 1H), 4.06 (br s, 1H), 3.72 (A of ABX, dd, JAB=11.5 Hz, JAX=3.9 Hz, 1H), 3.63 (B of ABX, dd, JAB=11.5 Hz, JBX=8.4 Hz, 1H), 3.30 (A of AB, d, J=13.5 Hz, 1H), 2.89 (B of AB, d, J=13.5 Hz, 1H), 1.48 (s, 9H), 1.03 (s, 3H).

Intermediate I.1.b.2 (Scheme 1.1)

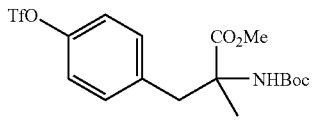

Prepared from alphamethyl p-tyrosine methyl ester using a similar procedure as described for the preparation of intermediate I.1.b.1 $^1$H NMR (400 MHz, $CDCl_3$) δ 7.08 (s, 4H), 5.17 (br s, 1H), 3.64 (s, 3H), 3.35 (A of AB, br d, J=13.4 Hz, 1H), 3.20 (B of AB, d, J=13.4 Hz, 1H), 1.43 (s, 3H), 1.38 (s, 9H).

Intermediate I.1.b.3 (Scheme 1.1)

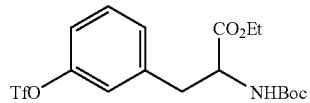

Prepared from m-tyrosine methyl ester using a similar procedure as described for the preparation of intermediate I.1.b.1. $^1$H NMR (400 MHz, $CDCl_3$) δ 7.38 (app. t, J=8.0 Hz, 1H), 7.21-7.14 (m, 2H), 7.06 (s, 1H), 5.04 (d, J=7.2 Hz, 1H), 4.62-4.54 (m, 1H), 4.23-4.10 (m, 2H), 3.19 (A of ABX, dd, JAB=13.7 Hz, JAX=5.8 Hz, 1H), 3.10 (B of ABX, dd, JAB=13.7 Hz, JBX=5.8 Hz, 1H), 1.43 (s, 9H), 1.24 (t, J=7.1 Hz, 3H).

Intermediate I.1.c.1 (Scheme 1.1)

Step A: Alkylation

To a solution of methyl N-(diphenylmethylene)alaninate (2.6 g, 9.7 mmol) in DMF (20 mL) cooled to 0° C. was added NaHMDS (12.2 mL, 12.2 mmol, 1M in THF) slowly via syringe and the reaction mixture was stirred at 0° C. for 15 min at which point 3-bromo-benzyl bromide (2.55 g, 10.2 mmol) in DMF (10 mL) was added slowly via syringe. The reaction mixture was allowed to warm to rt over 16 h, quenched with aq $NH_4Cl$ and water, extracted with EtOAc, washed with aq LiCl (×3), dried over $Na_2SO_4$, concentrated in vacuo, and purified by flash chromatography (120 g silica, 0-15% EtOAc in hexanes) to provide methyl 3-bromo-N-(diphenylmethylene)-α-methylphenylalaninate.

Step B: Deprotection

To a solution of methyl 3-bromo-N-(diphenylmethylene)-α-methylphenylalaninate (2.95 g, 6.76 mmol) in MeOH (25 mL) and THF (25 mL) was added 6N HCl (3.4 mL, 20.3 mmol) and the reaction mixture was stirred at RT for 5 min, concentrated in vacuo and purified by ion exchange chromatography (SCX, 25 g, then 50 g, MeOH then 2M $NH_3$ in MeOH) to provide methyl 3-bromo-α-methylphenylalaninate.

Step C: Boc Protection

To a solution of methyl 3-bromo-α-methylphenylalaninate (1.67 g, 6.1 mmol) in THF (30 mL) and MeOH (5 mL) was added ditertbutyldicarbonate (1.61 g, 7.4 mmol) and the reaction mixture was stirred at 50° C. for 6 h and at RT for 16 h, concentrated in vacuo, and purified by flash chromatography (90 g silica, 0-20% EtOAc in hexanes) to provide Intermediate I.1.c.1. $^1$H NMR (400 MHz, $CDCl_3$) δ 7.36 (d, J=7.6 Hz, 1H), 7.24 (s, 1H), 7.13 (t, J=7.6 Hz, 1H), 6.98 (d, J=7.6 Hz, 1H), 5.16 (br s, 1H), 3.77 (s, 3H), 3.39 (A of AB, br d, J=13.5 Hz, 1H), 3.19 (B of AB, d, J=13.5 Hz, 1H), 1.56 (br s, 3H), 1.49 (s, 9H).

Intermediate II.2.c.1 (Scheme 2.2)

Step A: Sulfonamide Installation

Methyl 2,6-dichloroisonicotinate (10 g, 48.5 mmol), methyl(propylsulfonyl)amine (7.99 g, 58.2 mmol), potassium phosphate (14.4 g, 68 mmol), Xantphos (1.69 g, 2.9 mmol)

and tris(dibenzylideneacetone)dipalladium (0.89 g, 0.97 mmol) were added to a dry, argon flushed flask. Dioxane (400 mL) was added, the solution degassed with argon and the reaction was heated to 100° C. for 16 hours. The reaction was cooled to rt, filtered through celite and evaporated in vacuo. Flash chromatography (silica, 0-35% EtOAc/hexanes) gave methyl 2-chloro-6-[(methylsulfonyl)(propyl)amino]isonicotinate as a yellow oil: $^1$H NMR (400 MHz, CD$_3$OD) δ 7.88 (s, 1H), 7.72 (s, 1H), 3.96 (s, 3H), 3.91 (t, J=6.4 Hz, 2H), 3.13 (s, 3H), 1.68-1.53 (m, 2H), 0.93 (t, J=7.5 Hz, 3H).

Step B: Reduction

To a solution of methyl 2-chloro-6-[(methylsulfonyl)(propyl)amino]isonicotinate (3.5 g, 11.5 mmol) in THF (50 mL) cooled to 0° C. was added LiBH$_4$ (17.2 mL, 34.4 mmol, 2 M in THF). After 10 min, the reaction mixture was allowed to warm to rt and stirred for 3.5 h. The reaction mixture was carefully quenched with EtOAc, MeOH and water. Following dilution with EtOAc, the organic layer was extracted, washed with brine, dried over sodium sulfate and concentrated in vacuo to provide N-[6-chloro-4-(hydroxymethyl)pyridin-2-yl]-N-propylmethanesulfonamide which was used as is in the bromination step.

Step C: Bromination

To a solution of N-[6-chloro-4-(hydroxymethyl)pyridin-2-yl]-N-propylmethanesulfonamide (740 mg, 2.65 mmol) in dichloromethane (20 mL) cooled to 0° C. was added carbon tetrabromide (967 mg, 2.92 mmol) and triphenylphosphine (765 mg, 2.92 mmol). After 10 min, the reaction mixture was allowed to warm to rt and stirred for 0.5 h. The reaction mixture was concentrated in vacuo and purified by flash chromatography (silica, 0-25% EtOAc/hexanes) to provide N-[4-(bromomethyl)-6-chloropyridin-2-yl]-N-propylmethanesulfonamide as a white solid. $^1$H NMR (400 MHz, CDCl$_3$) δ 7.34 (s, 1H), 7.22 (s, 1H), 4.35 (s, 2H), 3.85 (t, J=7.6 Hz, 2H), 3.04 (s, 3H), 1.64-1.50 (m, 2H), 0.93 (t, J=7.2 Hz, 3H).

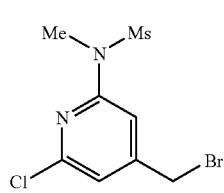

Intermediate II.2.c.2 (Scheme 2.2)

Synthesized using a procedure similar to that described for Intermediate II.2.c.1, with mesylmethylamine being used in the place of methyl(propylsulfonyl)amine in Step A.

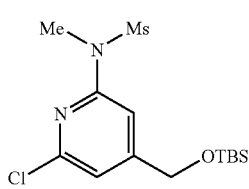

Intermediate II.2.f.1 (Scheme 2.2)

Step A: Sulfonamide Reduction

Performed as described in Step A of the synthesis of Intermediate II.2.c.1, with mesyl methyl sulfonamide being used in place of propyl methyl sulfonamide.

Step B: Reduction

Performed as described in Step B of the synthesis of Intermediate II.2.c.1.

Step C: Silyl Ether Formation

N-[6-chloro-4-(hydroxymethyl)pyridin-2-yl]-N-methylmethanesulfonamide (2.8 g, 11.1 mmol) from Step B, imidazole (0.91 g, 13.4 mmol), and tert-butyldimethylsilyl chloride (1.85 g, 12.2 mmol) were dissolved in anhydrous methylene chloride (25 mL) and allowed to stir at 25° C. for 16 hours. The solution was washed with 10% potassium monohydrogen sulfate (×2), saturated sodium bicarbonate (×2), water (×2), brine (×2), dried over sodium sulfate, and concentrated in vacuo. The resulting oil was purified by flash chromatography (145 g silica, 0-30% EtOAc in hexanes). The sample was taken to the next step without further purification. LC/MS [M+H]$^+$=365.1 (Cl pattern).

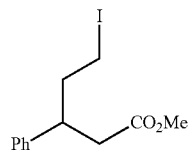

Intermediate III.5.b.1

Step A: Mono-Esterification of Diacid

3-Phenylglutaric acid (5 g, 24 mmol) and cesium carbonate (3.9 g, 12 mmol) were dissolved in 200 mL of anhydrous DMF and cooled to 0° C. Methyl iodide (1.5 mL, 24 mmol) was added via syringe to the solution, which was allowed to slowly warm to 25° C. over 16 hours. The reaction was diluted with water, and the pH was adjusted to ~9 with sat'd NaHCO3. The mixture was then washed with hexane (×7), acidified (pH ~4) with 1N HCl, extracted into ethyl acetate (×3), washed with LiCl (×3), dried over sodium sulfate and concentrated in vacuo. $^1$H NMR (400 MHz, CDCl$_3$) δ 7.3 (m, 2H), 7.2 (m, 3H), 3.65 (m, 1H), 3.60 (s, 3H), 2.7 (m, 4H).

Step B: Reduction of Acid 5-methoxy-5-oxo-3-phenylpentanoic acid (4.2 g, 19 mmol) was dissolved in 200 mL of anhydrous THF and cooled to 0° C. Borane (57 mL, 57 mmol, 1 M soln in THF) was added via syringe to the solution, which was allowed to slowly warm to 25° C. over 16 hours. The reaction was then cooled to 0° C. and quenched with methanol (25 mL), followed by water (25 mL), followed by saturated solution sodium bicarbonate (25 mL). The product was extracted into ethyl acetate, washed with brine, dried over sodium sulfate and concentrated in vacuo. The resulting oil and purified by flash chromatography (300 g silica, 10-65% EtOAc in hexanes). The sample was taken to the next step without further purification.

Step C: Iodination of Alcohol

Triphenylphosphine (1.5 g, 5.8 mmol) and imidazole (0.39 g, 5.8 mmol) were added to a dried flask under argon atmosphere. Anhydrous methylene chloride (50 mL) was added and the solution was cooled to 0° C. Iodine (1.45 g, 5.8 mmol) was added in one portion, and the resulting solution was stirred at 0° C. for 0.5 h. Methyl 5-hydroxy-3-phenylpentanoate (1.0 g, 4.8 mmol) in anhydrous methylene chloride (10 mL) was added via syringe to the solution and allowed to stir at 25° C. for 16 h. The solution was diluted with methylene chloride (100 mL), washed with 10% Na$_2$SO$_3$ (×2), brine (×2), dried over sodium sulfate, concentrated in vacuo. The resulting oil was purified by flash chromatography (175 g silica, 0-25% EtOAc in hexanes). The sample was taken to the next step without further purification. $^1$H NMR (400 MHz, CDCl$_3$) δ 7.3 (m, 2H), 7.2 (m, 3H), 3.7 (s, 3H), 3.30 (m, 1H), 3.15 (m, 1H), 2.85 (m, 1H), 2.65 (d, J=7.5 Hz, 2H), 2.25 (m, 1H), 2.15 (m, 1H).

Intermediate IV.1.b.1

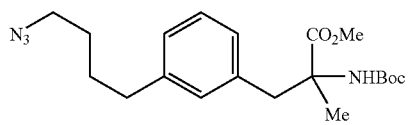

Step A: Suzuki Coupling

To 0.700 g (2.25 mmol, 1 equiv.) of (but-3-en-1-yloxy)(tert-butyl)diphenylsilane was added 5.9 mL (0.358 mmol, 1.3 equiv) of a 0.5M soln of 9-BBN in THF. The solution was heated to 70° C. for 1.25 h, then the reaction was cooled to rt, and transferred to a solution of Intermediate I.1.b.1 (0.995 g, 2.25 mmol, 1 equiv.) and Pd(Ph$_3$P)$_4$ (0.131 g, 0.113 mmol, 0.05 equiv.) in 1.05 mL 3.2M NaOH (3.38 mmol, 1.5 equiv.) and 3 mL toluene. The reaction was degassed with argon for 5 min, then capped and heated at 85° C. for 15 h. The reaction was cooled to rt and filtered through a pad of celite, rinsing with EtOAc. Partitioned filtrate between EtOAc and brine, separated and washed organics with brine, dried over Na$_2$SO$_4$, filtered and concentrated. Purified residue using silica gel chromatography to isolate desired product as a viscous oil. $^1$H NMR (400 MHz, CDCl$_3$) δ 7.63 (m, 4H), 7.42-7.32 (m, 6H), 7.14 (dd, J=7.6, 4.2 Hz, 1H), 7.00 (d, J=7.6 Hz, 1H), 6.87-6.84 (m, 2H), 3.70 (s, 3H), 3.64 (t, J=6.2 Hz, 2H), 3.28 (br peak, 1H), 3.13 (d, J=13.4 Hz, 1H), 2.55 (m, 1H), 2.39 (m, 1H), 1.89-1.76 (m, 2H), 1.69-1.54 (m, 2H), 1.53 (s, 3H), 1.39 (s, 9H), 1.02 (s, 9H). LC/MS [M+H]$^+$=604.

Step B: Silyl Deprotection

To solution of product from Step A (0.342 g, 0.566 mmol, 1 equiv) in 4 mL THF was added 0.736 mL (0.736 mmol, 1.3 equiv) of a 1M solution of tetra-n-butyl ammonium fluoride in THF. After 5 h, the reaction was quenched by the addition of satd. aqueous NaHCO$_3$ and diluted with EtOAc. The layers were separated, the aqueous was washed with fresh EtOAc, the combined organics were washed with brine, dried over Na$_2$SO$_4$, filtered and concentrated. Purified residue using silica gel chromatography to isolate desired product as a viscous oil. $^1$H NMR (400 MHz, CDCl$_3$) δ 7.14 (t, J=7.6 Hz, 1H), 7.00 (d, J=7.6 Hz, 1H), 6.87-6.84 (m, 2H), 3.70 (s, 3H), 3.60 (t, J=6.4 Hz, 2H), 3.30 (br peak, 1H), 3.13 (d, J=13.3 Hz, 1H), 2.58 (t, J=7.5 Hz, 2H), 1.69-1.45 (m, 7H), 1.45 (s, 9H). LC/MS [M+H]$^+$=366.

Step C: Bromination

To a solution of product from Step B (0.090 g, 0.246 mmol, 1.0 equiv), triphenylphosphine (0.129 g, 0.493 mmol, 2 equiv.) and imidazole (0.034 g, 0.493 mmol, 2 equiv) in 2.5 mL CH$_2$Cl$_2$ at 0° C. was added carbontetrabromide (0.163 g, 0.493 mmol, 2 equiv.). After 2.5 h, the bath was removed and after a further 2 h at rt, the reaction was poured onto a silica gel column for purification using normal phase chromatography. $^1$H NMR (400 MHz, CDCl$_3$) δ 7.16 (t, J=7.6 Hz, 1H), 7.02 (d, J=7.6 Hz, 1H), 6.89-6.87 (m, 2H), 3.73 (s, 3H), 3.38 (t, J=6.5 Hz, 2H), 3.31 (br peak, 1H), 3.14 (d, J=13.5 Hz, 1H), 2.57 (t, J=7.6 Hz, 2H), 1.86-1.82 (m, 2H), 1.76-1.69 (m, 2H), 1.54 (s, 3H), 1.45 (s, 9H). LC/MS [M+H]$^+$=428 (Br pattern).

Step D: Azide Displacement

To a solution of product from Step C (0.092 g, 0.215 mmol, 1 equiv) in 1.5 mL DMF was added sodium azide (0.028 g, 0.430 mmol, 2 equiv). After 15 h, the reaction was diluted with 3M LiCl and EtOAc. The layers were separated, and the organics were washed with 3M LiCl and brine, dried over Na$_2$SO$_4$, filtered and concentrated. Purification by normal phase chromatography afforded the desired azide (Intermediate IV.1.b.1) as a clear oil. $^1$H NMR (400 MHz, CDCl$_3$) δ 7.17 (t, J=7.5 Hz, 1H), 7.03 (d, J=7.6 Hz, 1H), 6.89-6.87 (m, 2H), 3.74 (s, 3H), 3.32 (br peak, 1H), 3.25 (t, J=6.6 Hz, 2H), 3.15 (d, J=13.4 Hz, 1H), 2.58 (t, J=7.2 Hz, 2H), 1.71-1.57 (m, 4H), 1.54 (s, 3H), 1.46 (s, 9H). LC/MS [(M-Boc)+H]$^+$=291.

Intermediate IV.1.d.1

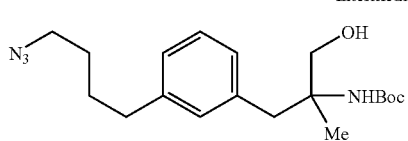

To a solution of Intermediate IV.1.c.1 (0.044 g, 0.113 mmol, 1 equiv) in 1.3 mL THF was added 2M LiBH$_4$ in THF (0.225 mL, 0.451 mmol, 4 equiv). After 16 h, the reaction was cooled to 0° C. and quenched by the addition of satd. aqueous NaHCO$_3$ and diluted with EtOAc. The layers were separated, the aqueous was washed with EtOAc (2×) the combined organics were washed with brine, dried over Na$_2$SO$_4$, filtered and concentrated. Purification by normal phase chromatography afforded the desired alcohol (Intermediate IV.1.d.1) as a clear oil. $^1$H NMR (400 MHz, CDCl$_3$) δ 7.20 (t, J=7.5 Hz, 1H), 7.04 (d, J=7.5 Hz, 1H), (6.98 (d, J=7.5 Hz, 1H), 6.97 (s, 1H), 4.05 (s, 1H), 4.17 (br s, 1H), 3.69-3.62 (m, 2H), 3.26 (t, J=6.8 Hz, 2H), 3.15 (d, J=13.3 Hz, 1H), 2.75 (d, J=13.4 Hz, 1H), 2.61 (t, J=7.3 Hz, 2H), 1.71-1.45 (m, 4H), 1.45 (s, 9H), 1.05 (s, 3H). LC/MS [(M-Boc)+H]$^+$=263.

Intermediate IV.1.e.1

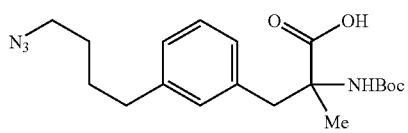

To a solution of Intermediate IV.1.c.1 (0.070 g, 0.179 mmol, 1 equiv) in 2 mL THF was added 1M LiOH in THF (0.538 mL, 0.538 mmol, 3 equiv). After 3 h, 0.5 mL MeOH was added, and after 15 h, the reaction was heated to 45° C. for 4.5 h. The reaction was cooled to rt and acidified to pH 3 using 10% KHSO$_4$. The aqueous was washed with EtOAc (4×) the combined organics were dried over Na2SO4, filtered and concentrated. The residue was used without further purification. $^1$H NMR (400 MHz, CDCl$_3$) δ 9.92 (br s, 1H), 7.18 (t, J=7.5 Hz, 1H), 7.05 (d, J=7.5 Hz, 1H), 6.97-6.94 (m, 2H), 5.05 (br s, 1H), 3.26 (t, J=6.7 Hz, 4H), 2.59 (t, J=7.3 Hz, 2H), 1.72-1.58 (m, 4H), 1.55 (s, 3H), 1.47 (s, 9H). LC/MS [(M-Boc)+H]$^+$=277.

Intermediate 5.2.a.1

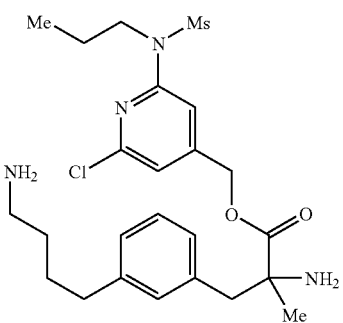

Step A: Coupling

To a solution of Intermediate IV.1.e.1 (0.077 g, 0.205 mmol, 1 equiv) and Intermediate II.2.c.1 (0.070 g, 0.205 mmol, 1 equiv.) in 1.5 mL DMF was added CsCO₃ (0.080 g, 0.245 mmol, 1.2 equiv.). After 1.5 h, the reaction was partitioned between H₂O and EtOAc, the layers were separated, the organics were washed with 3M LiCl (2×) and brine, dried over Na₂SO₄, filtered and concentrated. The residue was purified by normal phase silica gel chromatography to afford the desired product as a clear oil. ¹H NMR (400 MHz, CDCl₃) δ 7.26 (s, 1H), 7.17 (d, J=7.5 Hz, 1H), 7.12 (s, 1H), 7.06 (d, J=7.5 Hz, 1H), 6.90-6.89 (m, 2H), 5.17 (d, J=14.3 Hz, 1H), 5.09 (d, J=14.3 Hz, 1H), 4.90 (br s, 1H), 3.82 (t, J=7.2 Hz, 2H), 3.32-3.24 (m, 3H), 3.16 (d, J=13.6 Hz, 1H), 3.01 (s, 3H), 2.58 (t, J=7.1 Hz, 2H), 1.69-1.54 (m, 6H), 1.49 (s, 3H), 1.44 (s, 9H), 0.90 (t, J=7.5 Hz, 3H). LC/MS [(M-tBu)+H]⁺=581.

Step B: Staudinger Reduction

To a solution of product from Step A (0.040 g, 0.063 mmol) in 1 mL THF and 0.1 mL water was added triphenylphosphine (0.026 g, 0.10 mmol). The reaction was heated at 65° C. for 1.5 h, cooled to rt, then pipetted onto a 1 g SCX ion exchange column conditioned with MeOH. The column was eluted with 50 mL MeOH, them 50 mL 2M NH3 in MeOH. The fractions containing the desired product were collated and concentrated. LC/MS [M+H]⁺=611 (Cl pattern).

Intermediate 5.2.a.2

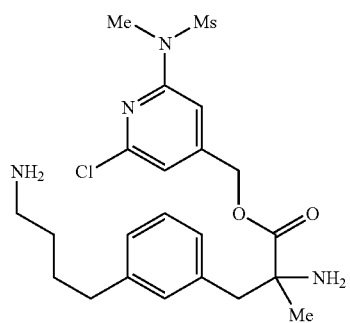

Synthesized using a reaction sequence similar to that described for the synthesis of Intermediate V.2.a.2, with Intermediate II.2.c.2 being used in place of Intermediate II.c.1 in step A.

Intermediate V.11.b.1

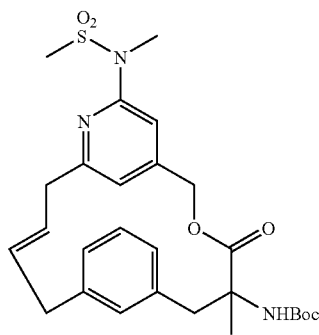

Step A: Hydrolysis

Performed on Intermediate I.1.c.1 as described for the synthesis of intermediate IV.e.1. LC/MS [M+H]=358, 360 (Br pattern)

Step B: Coupling

Product from Step A and Intermediate 2.2.e.2 were coupled as described in Step A of Intermediate V.2.a.1 synthesis. LC/MS [M+H]=590, 592 (Br pattern)

Step C: Allylation

To a solution of {2-chloro-6-[methyl(methylsulfonyl)amino]pyridine-4-yl}methyl 3-bromo-N-(tert-butoxycarbonyl)-α-methylphenylalaninate (400 mg, 0.68 mmol) and allyltributylstannane (0.48 mL, 1.6 mmol) in degassed DMF (4 mL) was added bis(triphenylphosphine)palladium(II) dichloride (33 mg, 0.048 mmol). The reaction was heated to 120° C. in a microwave for 0.5 h. Additional catalyst was added and heating was repeated 3× to drive the reaction to completion. Potassium fluoride (134 mg, 2.3 mmol) was added, the reaction was stirred for 3 h and diluted with EtOAc. Filtration through celite, concentration and flash chromatography (silica gel, 0-50% EtOAc/hexanes) gave {2-allyl-6-[methyl(methylsulfonyl)amino]pyridine-4-yl}methyl 3-allyl-N-(tert-butoxycarbonyl)-α-methylphenylalaninate. MS: 558.1 (M+1) ES+

Step D: Ring Closing Metathesis Reaction

To a solution of {2-allyl-6-[methyl(methylsulfonyl)amino]pyridine-4-yl}methyl 3-allyl-N-(tert-butoxycarbonyl)-α-methylphenylalaninate (80 mg, 0.14 mmol) in degassed DCE (2.9 mL) was added Zhan (metathesis) Catalyst I (9.2 mg, 0.014 mmol). The reaction was heated to 120° C. in a microwave for 0.5 h. Concentration and flash, chromatography (silica gel, 0-50% EtOAc/hexanes) gave tert-butyl [(3EZ)-14-methyl-8-[methyl(methylsulfonyl)amino]-13-oxo-12-oxa-7-azatricyclo[14.3.1.1⁶,¹⁰]henicosa-1(20),3,6(21),7,9,16,18-heptaen-14-yl]carbamate. MS: 530.4 (M+1) ES+

Example 1

N-[13-amino-13-methyl-15-oxa-2,20-diazatricyclo[15.3.1.1⁷,¹¹]docosa-1(21),7(22),8,10,17,19-hexaen-19-yl]-N-propylmethanesulfonamide

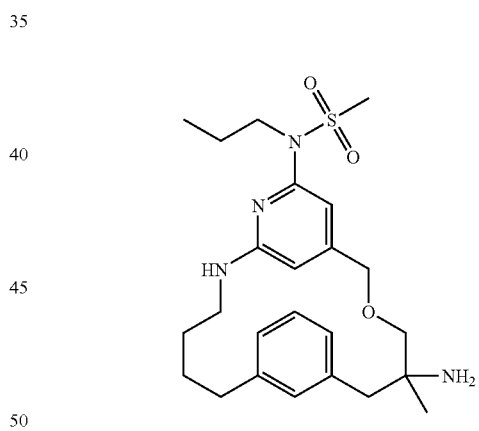

Step A: Coupling

To a solution of Intermediate IV.1.d.1 (0.039 g, 0.109 mmol, 1.2 equiv) and Intermediate II.2.c.1 (0.031 g, 0.091 mmol, 1 equiv.) in 1.5 mL 1,2-dichloroethane was added a spatula tip of activated 4 A molecular sieves, polymer bound 2,6-di-tBuPy (0.052 g, 0.272 mmol, 3 equiv.) and AgOTf (0.068 g, 0.263 mmol, 2.9 equiv.). The solution was microwaved at 90° C. for 8.5 h, then filtered through a pad of celite, rinsing with EtOAc. The rinsate was concentrated, and the residue was purified by normal phase silica gel chromatography. ¹H NMR (400 MHz, CDCl₃) δ 7.20-7.16 (m, 2H), 7.03 (d, J=7.5 Hz, 1H), 6.8-6.96 (m, 3H), 4.53 (s, 2H), 4.47 (s, 1H), 3.81 (t, J=7.3 Hz, 2H), 3.65 (d, J=9.0 Hz, 1H), 3.52 (d, J=9.0 Hz, 1H), 3.25 (t, J=6.7 Hz, 2H), 3.11 (d, J=13.2 Hz, 1H), 3.00 (s, 3H), 2.85 (d, J=13.2 Hz, 1H), 2.59 (t, J=7.1 Hz, 2H), 1.70-1.52 (m, 6H), 1.45 (s, 9H), 1.23 (s, 3H), 0.90 (t, J=7.3 Hz, 3H). LC/MS [M+H]⁺=623.

Step B: Staudinger Reduction

To a solution of product from Step A (0.020 g, 0.032 mmol, 1 equiv) in 0.70 mL THF and 0.070 mL water was added triphenylphosphine (0.009 g, 0.035 mmol, 1.1 equiv.). The reaction was heated at 65° C. for 15 h, cooled to rt, then pipetted onto a 1 g SCX ion exchange column conditioned with MeOH. The column was eluted with 50 mL MeOH, then 50 mL 2M NH3 in MeOH. The fractions containing the desired product were collated and concentrated. $^1$H NMR (400 MHz, CDCl$_3$) δ 7.19-7.16 (m, 2H), 7.04 (d, J=7.5 Hz, 1H), 6.96-6.95 (m, 3H), 4.54 (s, 2H), 4.52 (s, 1H), 3.81 (t, J=7.1 Hz, 2H), 3.65 (d, J=9.0 Hz, 1H), 3.52 (d, J=9.0 Hz, 1H), 3.11 (d, J=13.2 Hz, 1H), 3.01 (s, 3H), 2.84 (d, J=13.2 Hz, 1H), 2.68 (t, J=7.0 Hz, 2H), 2.58 (t, J=7.7 Hz, 2H), 1.66-1.48 (m, 6H), 1.45 (s, 9H), 1.23 (s, 3H), 0.91 (t, J=7.4 Hz, 3H). LC/MS [M+H]$^+$=597.

Step C: Macroamination

To a solution of product from Step B (0.015 g, 0.025 mmol, 1 equiv) in 0.60 mL DMA was added K$_3$PO$_4$ (0.016 g, 0.075 mmol, 3 equiv.) and Pd(t-Bu3)$_2$ (0.004 g, 0.008 mmol, 0.3 equiv). The reaction was degassed with Ar, then heated at 100° C. for 19 h, cooled to rt and diluted with H2O and EtOAc. The layers were separated, and the organics were washed with 3M LiCl (2×) and brine, dried over Na$_2$SO$_4$, filtered and concentrated. The residue was purified using silica gel chromatography to obtain the desired product was a clear glass. $^1$H NMR (400 MHz, CDCl$_3$) δ 7.10 (t, J=8.0 Hz, 1H) 6.95-6.94 (m, 3H), 6.39 (s, 1H), 6.05 (s, 1H), 4.84 (s, 1H), 4.73 (t, J=6.4 Hz, 1H), 4.50 (d, J=13.5 Hz, 1H), 4.31 (d, J=13.5 Hz, 1H), 3.65 (t, J=6.3 Hz, 2H), 3.35-3.19 (m, 4H), 3.02 (d, J=9.3 Hz, 1H), 2.97 (s, 3H), 2.67 (d, J=9.3 Hz, 1H), 2.61 (m, 1H), 1.67 (m, 2H), 1.56-1.48 (m, 6H), 1.48 (s, 9H), 1.24 (s, 3H), 0.86 (t, J=7.5 Hz, 3H). LC/MS [M+H]$^+$=561.

Step D: Boc Deprotection

To a solution of product from Step C (0.004 g, 0.007 mmol, 1 equiv) in 1.0 mL CH$_2$Cl$_2$ was added 4M HCl in dioxane (0.027 mL, 0.107 mmol, 15 equiv.). After 15 h at rt, the reaction was concentrated to afford the hydrochloride salt of N-[13-amino-13-methyl-15-oxa-2,20-diazatricyclo[15.3.1.17,11]docosa-1(21),7(22),8,10,17,19-hexaen-19-yl]-N-propyl methanesulfonamide as a white solid. $^1$H NMR (400 MHz, d$_4$-MeOH) δ 7.21 (t, J=7.5 Hz, 1H), 7.10 (d, J=7.5 Hz, 1H), 7.01 (d, J=7.5 Hz, 1H), 6.97 (s, 1H), 6.77 (s, 1H), 6.76 (s, 1H), 4.75 (d, J=13.9 Hz, 1H), 4.52 (d, J=13.9 Hz, 1H), 3.72-3.54 (m, 4H), 3.45-3.33 (m, 2H), 3.12 (d, J=10.4 Hz, 1H), 2.79 (d, J=10.3 Hz, 1H), 2.70-2.56 (m, 2H), 1.73-1.44 (m, 6H), 1.27 (s, 3H), 0.88 (t, J=7.4 Hz, 3H). LC/MS [M+H]$^+$=461. Exact Mass calc for C$_{24}$H$_{36}$N$_4$O$_3$S: 461.2581; measured: 461.2567.

Example 2

N-[13-amino-13-methyl-14-oxo-15-oxa-2,20-diazatricyclo[15.3.1.17,11]docosa-1(21),7(22),8,10,17,19-hexaen-19-yl]-N-propylmethanesulfonamide

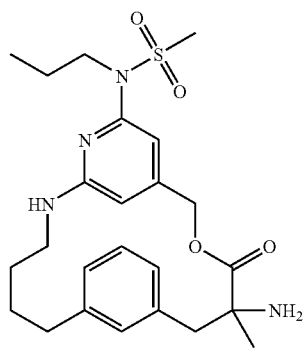

Step A: Macroamination

Performed on Intermediate 5.2.a.1 described in Step C of the Example 1 synthesis, with the following modifications: 2 equiv. of K$_3$PO$_4$ were used, and the reaction was heated at 90° C. for 2 h.

Step B: Boc Deprotection

Performed as described in Step D of the Example 1 synthesis. $^1$H NMR (400 MHz, d$_4$-MeOH) δ 7.16 (t, J=7.5 Hz, 1H), 7.05 (d, J=7.5 Hz, 1H), 6.90 (d, J=7.5 Hz, 1H), 6.59 (s, 1H), 6.29 (br s, 1H), 6.23 (s, 1H), 5.20 (d, J=12.3 Hz, 1H), 5.01 (d, J=12.3 Hz, 1H), 3.69 (m, 2H), 3.40 (m, 2H), 3.16 (d, J=13.9 Hz, 1H), 3.04-2.97 (m, 3H), 2.49 (m, 2H), 1.64 (s, 3H), 1.61-1.43 (m, 6H), 0.83 (t, J=7.3 Hz, 3H). LC/MS [M+H]$^+$=475. Exact Mass calc for C$_{24}$H$_{34}$N$_4$O$_4$S: 475.2374; measured: 475.2384.

Example 3

N-[13-amino-13-methyl-14-oxo-15-oxa-2,20-diazatricyclo[15.3.1.17,11]docosa-1(21),7(22),8,10,17,19-hexaen-19-yl]-N-methylmethanesulfonamide

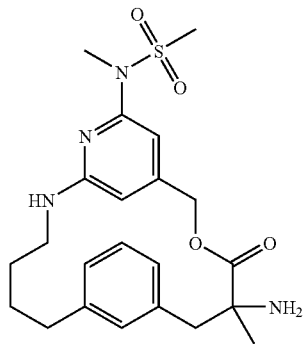

Prepared from Intermediate 5.2.a.2 utilizing a reaction sequence as described for the synthesis of Example 2.

Example 4

N-[13-amino-2-benzyl-13-methyl-14-oxo-15-oxa-2,20-diazatricyclo[15.3.1.1$^{7,11}$]docosa-1(21),7(22),8,10,17,19-hexaen-19-yl]-N-methylmethanesulfonamide

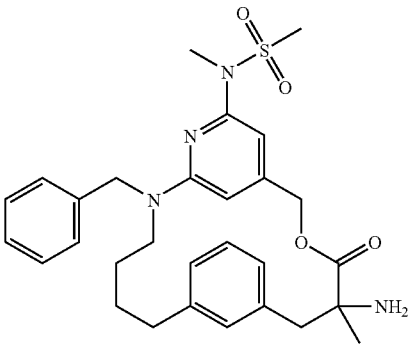

Step A: Reductive Amination

To a solution of Intermediate 5.2.a.2 (0.030 g, 0.051 mmol) in 0.4 mL 1,2-dichloroethane was added benzaldehyde (0.006 mL, 0.057 mmol), sodium triacetoxyborohydride (0.014 g, 0.067 mmol) and acetic acid (1 drop). The reaction was allowed to proceed overnight, then contrated and purified by reverse-phase Gilson. LC/MS [M+H]+=673 (Cl pattern).

Step B and Step C: Macroamination and Boc Deprotection

Performed as described for the synthesis of Example 3. LC/MS [M+H]$^+$ for title compound=537.

The following compounds were synthesized using a procedure as described for the synthesis of Example 4.

| Red. Amin Partner | Example | Structure | LC/MS (M + H)$^+$ |
|---|---|---|---|
| Acetone | 5 | 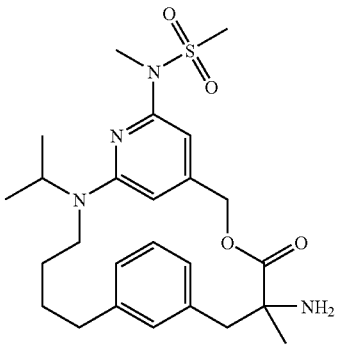 | 488 |
| Propanal | 6 | 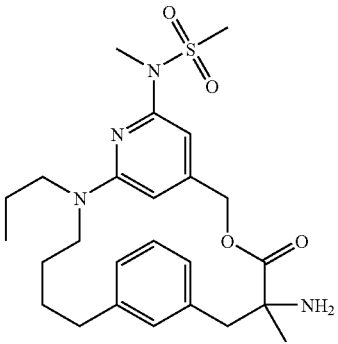 | 488 |
| Cyclopropyl carboxaldehyde | 7 | 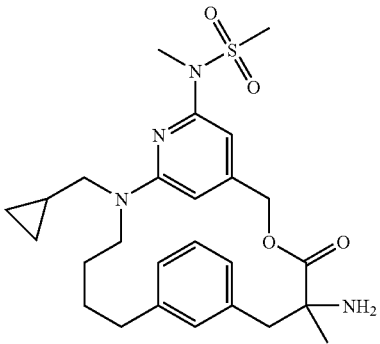 | 500 |

Example 8

5-methyl-19-[methyl(methylsulfonyl)amino]-4-oxo-14-phenyl-3-oxa-18-azatricyclo[15.3.1.1~7,11~]docosa-1(21),7(22),8,10,17,19-hexaen-5-amine

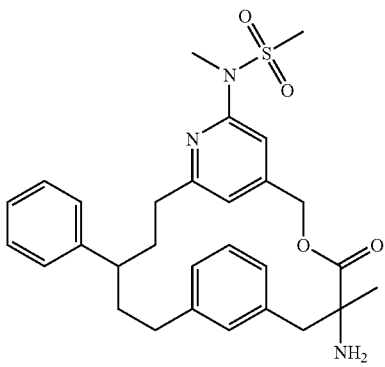

Step A: Zincate Coupling of Intermediate A and B

Intermediate III.5.b.1 (1.0 g, 3.14 mmol) and activate zinc (0.225 g, 3.45 mmol) was dissolved in degassed THF (8 mL) and allowed to stir under argon at 25° C. for 3 h. The iodide/activated zinc mixture was added via syringe to a dried flask containing intermediate II.2.f.1 (1.15 g, 3.14 mmol) and [(t-Bu)$_3$P]$_2$Pd (0.16 g, 0.314 mmol) in degassed THF (15 mL) under argon atmosphere. The resulting solution was stirred at 75° C. for 16 h. The solution was then filtered over a pad of celite, washing with ethyl acetate, and concentrated in vacuo. The resulting oil was purified by flash chromatography (175 g silica, 0-25% EtOAc in hexanes). The sample was taken to the next step without further purification. LC/MS [M+H]$^+$=520.1.

Step B: Reduction of Ester methyl 5-{4-({[tert-butyl(dimethyl)silyl]oxy}methyl)-6-{methyl(methylsulfonyl)amino]pyridin-2-yl}-3-phenylpentanoate (0.55 g, 1.05 mmol) from step A was dissolved in anhydrous THF (10 mL) and cooled to 0° C. under argon atmosphere. Lithium borohydride (0.74 mL, 1.49 mmol, 2.0 M solution in THF) was slowly added via syringe. After addition was complete, the temperature was raised to 45° C. and the reaction was allowed to stir at that temperature for 16 h. The solution was then cooled to 0° C. and quenched with methanol (5 mL) followed by water (5 mL). The product was extracted into ethyl acetate, washed with brine, dried over sodium sulfate and concentrated in vacuo. The sample was taken to the next step without further purification. LC/MS [M+H]$^+$=493.0

Step C: Iodination of Alcohol

Prepared in a similar fashion as the preparation of Intermediate III.5.b.1, Step C.

Step D: Zincate Coupling of Intermediate I.1.c.1 and Scaffold

N-[4-({[tert-butyl(dimethyl)silyl]oxy}methyl)-6-(5-iodo-3-phenylpentyl)pyridin-2-yl]-N-methylmethanesulfonamide (0.395 g, 0.66 mmol) from Step C and activated zinc (0.086 g, 1.3 mmol) was dissolved in degassed THF (2 mL) and allowed to stir under argon at 25° C. for 3 h. The iodide/activated zinc mixture was added via syringe to a dried flask containing intermediate I.1.c.1 (0.244 g, 0.66 mmol) and [(t-Bu)$_3$P]$_2$Pd (0.033 g, 0.066 mmol) in degassed THF (5 mL) under argon atmosphere. The resulting solution was stirred at 75° C. for 16 h. The solution was then filtered over a pad of celite, washing with ethyl acetate, and concentrated in vacuo. The resulting oil was purified by flash chromatography (90 g silica, 0-20% EtOAc in hexanes). The sample was taken to the next step without further purification. LC/MS [M+H]$^+$=768.2

Step E: Silyl Deprotection

To solution of product from Step D (0.118 g, 0.154 mmol) in 2 mL THF was added 0.169 mL (0.169 mmol) of a 1M solution of tetra-n-butyl ammonium fluoride in THF. After 5 h, the reaction was quenched by the addition of satd. aqueous NaHCO$_3$ and diluted with EtOAc. The layers were separated, the aqueous was washed with fresh EtOAc, the combined organics were washed with brine, dried over Na$_2$SO$_4$, filtered and concentrated. Purified residue using silica gel chromatography to isolate desired product as a viscous oil. LC/MS [M+H]$^+$=654.1

Step F: Hydrolysis of Ester

To solution of product from Step E (0.038 g, 0.058 mmol) in 2 mL THF was added 0.145 mL (0.291 mmol) of a 1M solution of LiOH in water. The solution was allowed to stir overnight at 45° C. for 16 h. The crude reaction mixture was acidified to pH=4 using 1M HCl, extracted into ethyl acetate, washed with 3 M solution of LiCl and dried over sodium sulfate. The solvent was removed in vacuo and taken to the next step without further purification. LC/MS [M+H]$^+$=640.2

Step G: Mitsonobu Macrolactionization

To a solution of the product from Step F (0.035 g, 0.055 mmol) and triphenylphosine (0.022 g, 0.082 mmol) in 6 mL of anhydrous THF under argon atmosphere was added DIAD (0.016 mL, 0.082 mmol) via syringe. The solution was allowed to stir at 25° C. for 3 h. The solution was then concentrated and purified residue using reverse phase (C18) chromatography to isolate desired product as a viscous oil. LC/MS [M+H]$^+$=622.0.

Step H: Boc Deprotection

To a solution of product from Step H (0.028 g, 0.045 mmol) in 1.0 mL CH$_2$Cl$_2$ was added 4M HCl in dioxane (0.027 mL, 0.107 mmol). After 15 h at rt, the reaction was concentrated to afford the hydrochloride salt of 5-methyl-19-[methyl(methylsulfonyl)amino]-4-oxo-14-phenyl-3-oxa-18-azatricyclo[15.3.1.1~7,11~]docosa-1(21),7(22),8,10,17,19-hexaen-5-aminium chloride as a white solid. LC/MS [M+H]$^+$=522.0. Exact Mass calc for C$_{29}$H$_{35}$N$_3$O$_4$S: 522.2421; measured: 522.2418.

Example 9

5-methyl-19-[methyl(methylsulfonyl)amino]-3,4-dioxa-18-azatricyclo[15.3.1.1~7,11~]docosa-1(21),7(22),8,10,17,19-hexaen-5-amine

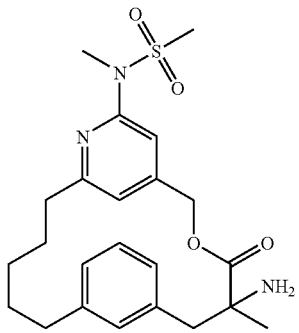

Step A: Suzuki Coupling

To 5.28 mL (50.4 mmol) of 1,4-pentadiene was added 14.8 mL (7.4 mmol) of a 0.5 M solution of 9-BBN in THF. The solution was heated to 70° C. for 1.25 h, then the reaction was cooled to rt, and transferred to a solution of Intermediate I.1.c.1 (2.5 g, 6.7 mmol), Pd(Ph$_3$P)$_4$ (0.77 g, 0.67 mmol) in 2.2 mL 3.2M NaOH (7.05 mmol) and 10 mL of degassed toluene. The reaction was then degassed with argon for 5 min, then capped and heated at 85° C. for 15 h. The reaction was cooled to rt and filtered through a pad of celite, rinsing with EtOAc. Partitioned filtrate between EtOAc and brine, separated and washed organics with brine, dried over Na$_2$SO$_4$, filtered and concentrated. Purified residue using silica gel chromatography to isolate desired product as a viscous oil. LC/MS [M+H]$^+$=362.1.

Step B: Suzuki with Product from Step A and Intermediate 2.2f

Prepared as described in Step A.

Step C-F: Silyl Deprotection, Ester hydrolysis, Mitsunobu macrolactonization and Boc deprotection sequence performed as described in the synthesis of Example 9. LC/MS [M+H]=446

Example 10

5-methyl-19-[methyl(methylsulfonyl)amino]-4-oxo-14-methyl-3-oxa-18-azatricyclo[15.3.1.1~7,11~]docosa-1(21),7(22),8,10,17,19-hexaen-5-amine

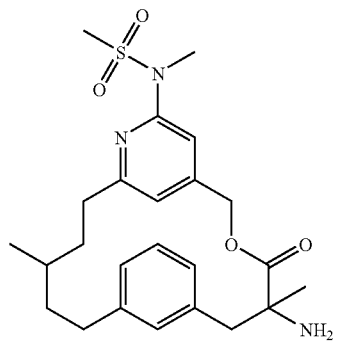

Synthesized using a reaction sequence similar to that described for Example 9, with 3-methyl-1,4-pentadiene being substituted for 1,4-pentadiene in Step A. LC/MS [M+H]=460.

Example 11

N-[(15E)-5-amino-5,14-dimethyl-4-oxo-3-oxa-18-azatricyclo[15.3.1.1$^{7,11}$]docosa-1(21),7(22),8,10,15,17,19-heptaen-19-yl]-N-methylmethanesulfonamide

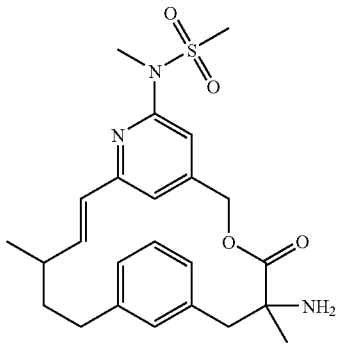

Step A: Suzuki with 3-Methyl-1,4-pentadiene and I.1.c.1
Prepared as Step A in the synthesis of Example 9.
Step B: Hydrolysis of Ester
Prepared as Step F in synthesis of Example 9.
Step C: Alkylation To a solution of the product of Step B (0.515 g, 1.425 mmol) and II.2.c.2 (0.491 g, 1.55 mmol) in DMF (7 mL) was added cesium carbonate (0.302 g, 0.926 mmol). The reaction was allowed to stir at rt for 16 h. The crude mixture was extracted with EtOAc (×3), washed with DI water (×3), sated LiCl (×3), dried over sodium sulfate, and concentrated in vacuo. The crude material was purified using flash chromatography (90 g silica, 0-25% EtOAc in hexanes) to afford the corresponding lactone.

Step D: Intramolecular Heck Reaction

To a solution of product from Step C (0.10 g, 0.17 mmol) and potassium phosphate (0.107 g, 0.51 mmol) in 8 mL of degassed anhydrous DMA under argon atmosphere was added [(t-Bu)$_3$P]$_2$Pd (0.009 g, 0.017 mmol). The whole system was then degassed with argon. The temperature was raised to 115° C. and allowed to stir at that temperature for 16 h. The crude reaction was filtered over celite, washing with ethyl acetate. The organic layers were washed with water (×3), brine (×3), dried over sodium sulfate, solvent was removed in vacuo. The resulting oil was purified by flash chromatography (40 g silica, 0-25% EtOAc in hexanes). The sample was taken to the next step without further purification. LC/MS [M+H]$^+$=558.1

Step E: Boc Deprotection

Prepared as Step H in synthesis of Example 8. LC/MS [M+H]$^+$=458.1

Example 12

N-[14-amino-4,14-dimethyl-5-methylene-13-oxo-12-oxa-7-azatricyclo[14.3.1.1$^{6,10}$]henicosa-1(20),6(21),7,9,16,18-hexaen-8-yl]-N-methylmethanesulfonamide

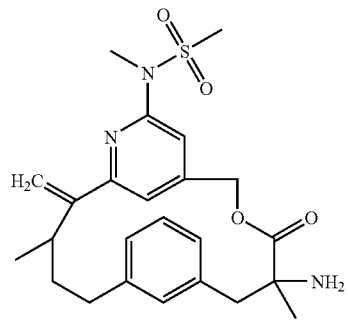

Isolated as a secondary product in Step D of the Example 11 synthesis elaborated through step E to afford title compound. LC/MS [M+H]$^+$=458.1.

Example 13

N-[(3E)-14-Amino-14-methyl-13-oxo-12-oxa-7-azatricyclo[14.3.1.1$^{6,10}$]henicosa-1(20),3,6(21),7,9,16,18-heptaen-8-yl]-N-methylmethanesulfonamide and N-[(3Z)-14-Amino-14-methyl-13-oxo-12-oxa-7-azatricyclo[14.3.1.1$^{6,10}$]henicosa-1(20),3,6(21),7,9,16,18-heptaen-8-yl]-N-methylmethanesulfonamide

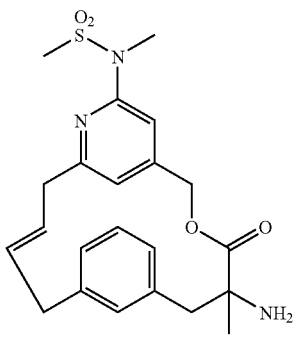

A solution of tert-butyl [(3EZ)-14-methyl-8-[methyl(methylsulfonyl)amino]-13-oxo-12-oxa-7-azatricyclo[14.3.1.1^{6,10}]henicosa-1(20),3,6(21),7,9,16,18-heptaen-14-yl]carbamate (14 mg, 0.026 mmol) (Intermediate V.11.c.1) in DCM (0.5 mL) and TFA (1.5 mL) was stirred at rt for 1 h. Concentration, purification and separation of EZ isomers by reverse phase preparative HPLC (5-95% CH$_3$CN in water containing 0.1% TFA) gave N-[(3E)-14-Amino-14-methyl-13-oxo-12-oxa-7-azatricyclo[14.3.1.1^{6,10}]henicosa-1(20),3,6(21),7,9,16,18-heptaen-8-yl]-N-methylmethanesulfonamide and N-[(3Z)-14-Amino-14-methyl-13-oxo-12-oxa-7-azatricyclo[14.3.1.1^{6,10}]henicosa-1(20),3,6(21),7,9,16,18-heptaen-8-yl]-N-methylmethanesulfonamide as the TFA salts. Exact Mass calc for (E or Z) C$_{22}$H$_{27}$N$_3$O$_4$S: 430.1795; measured: 430.1798. Exact Mass calc for (Z or E) C$_{22}$H$_{27}$N$_3$O$_4$S: 430.1795; measured: 430.1801.

Example 14

N-[14-Amino-14-methyl-13-oxo-12-oxa-7-azatricyclo[14.3.1.1^{6,10}]henicosa-1(20),6(21),7,9,16,18-hexaen-8-yl]-N-methylmethanesulfonamide

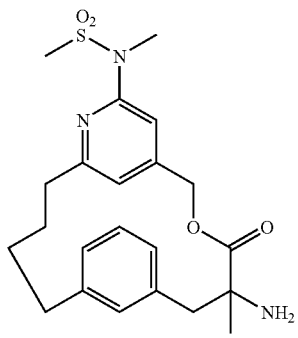

Step A: Olefin Reduction

To a solution of tert-butyl [(3EZ)-14-methyl-8-[methyl(methylsulfonyl)amino]-13-oxo-12-oxa-7-azatricyclo[14.3.1.1^{6,10}]henicosa-1(20),3,6(21),7,9,16,18-heptaen-14-yl]carbamate (22.5 mg, 0.042 mmol) (Intermediate V.11.c.1) in degassed THF (2.5 mL) was added palladium on carbon (10%, 3 mg). The reaction was stirred under a hydrogen atmosphere (1 atm) for 1 h and filtered through celite. Concentration gave tert-butyl [14-methyl-8-[methyl(methylsulfonyl)amino]-13-oxo-12-oxa-7-azatricyclo[14.3.1.1^{6,10}]henicosa-1(20),6(21),7,9,16,18-hexaen-14-yl]carbamate. MS: 532.0 (M+1) ES+

Step B: Boc Deprotection

A solution of tert-butyl [14-methyl-8-[methyl(methylsulfonyl)amino]-13-oxo-12-oxa-7-azatricyclo[14.3.1.1^{6,10}]henicosa-1(20),6(21),7,9,16,18-hexaen-14-yl]carbamate (22 mg, 0.041 mmol) in DCM (0.5 mL) and TFA (0.5 mL) was stirred at rt for 1.5 h. Concentration and purification by reverse phase preparative HPLC (5-95% CH$_3$CN in water containing 0.1% TFA) gave N-[14-amino-14-methyl-13-oxo-12-oxa-7-azatricyclo[14.3.1.1^{6,10}]henicosa-1(20),6(21),7,9,16,18-hexaen-8-yl]-N-methylmethanesulfonamide as the TFA salt. Exact Mass calc for C$_{22}$H$_{29}$N$_3$O$_4$S: 432.1952; measured: 432.1956.

Example 15

N-[13-amino-18-chloro-13-methyl-14-oxo-15-oxa-2,20-diazatricyclo[15.3.1.1^{7,11}]docosa-1(21),7(22),8,10,17,19-hexaen-19-yl]-N-methylmethanesulfonamide

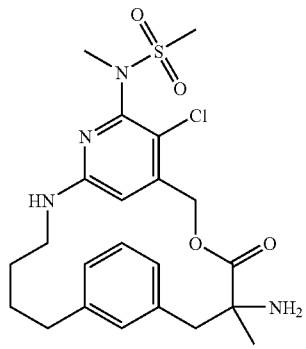

To a solution of Example 3 (0.440 g, 0.785 mmol) in 13 mL CH$_2$Cl$_2$ was added NCS (0.105 g, 0.785 mmol), and the reaction was allowed to proceed at rt for 4 days. The reaction was concentrated and purified by preparative HPLC to afford the title compound. LC/MS [M+H]$^+$=481.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula (II):

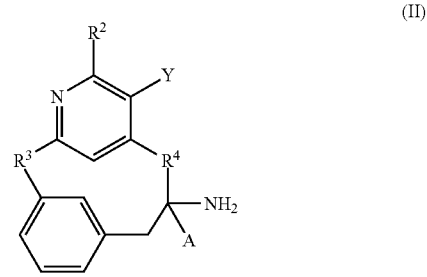

wherein:
Y is selected from the group consisting of
(1) hydrogen,
(2) —C$_{1-3}$ alkyl, wherein said alkyl is optionally substituted with one or more halogen,
(3) halogen, and
(4) cyano;

A is selected from the group consisting of
(1) hydrogen,
(2) —$C_{1-10}$ alkyl,
$R^2$ is selected from the group consisting of:
(1) ($R^5$—$SO_2$)N($R^6$)—, wherein $R^5$ is
  (a) —$C_{1-10}$ alkyl,
  wherein said alkyl is unsubstituted or substituted with one or more
  (i) halo,
  (ii) —OH,
  (iii) —CN,
  (iv) —O—$C_{1-10}$ alkyl, and
  (v) —$C_{1-10}$ alkyl;
$R^6$ is selected from the group consisting of
  (a) hydrogen,
  (b) —$C_{1-10}$ alkyl, and
  (e) —$C_{6-10}$ aryl
  wherein said alkyl, is unsubstituted or substituted with one or more
  (i) halo,
  (ii) —OH,
  (iii) —CN,
  (iv) —O—$C_{1-10}$ alkyl,
$R^3$ is

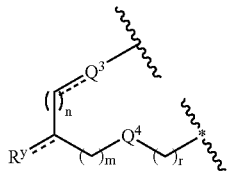

wherein if the dotted line leading to $Q^3$ is absent, then $Q^3$ is selected from the group consisting of
(a) —$CH_2$—
(c) —$NR^x$—,
  wherein $R^x$ is selected from the group consisting of
  (i) hydrogen,
  (ii) —$C_{1-10}$ alkyl,
  (v) —$C_{3-8}$ cycloalkyl,
  (vi) —$C_{0-6}$ alkylene-$C_{6-10}$ aryl, and
  (viii) —$CO_{0-6}$ alkyl-$C_{3-8}$ cycloalkyl,
and if the dotted line leading to $Q^3$ represents a bond, then $Q^3$ is —CH— or —$CH_2$—CH—,
if the dotted line leading to $R^y$ is absent, then $R^y$ is selected from the group consisting of
(a) hydrogen,
(b) —$C_{1-10}$ alkyl,
and if the dotted line leading to $R^y$ represents a bond, then $R^y$ is selected from the group consisting of
(a) =CH—$C_{1-10}$ alkyl,
(b) =CH—$C_{0-6}$ alkyl-$C_{6-10}$ aryl,
$Q^4$ is —$CH_2$:
$R^4$ is —$(CH_2)_s$-$Q^2$-$(CH_2)_t$, wherein $Q^2$ is selected from the group consisting of
(1) —O—
(2) —O—C(=O)—, and
(3) —C(=O)—O—,
m is 1;
n is 1;
r is 0;
s is 1; and
t is 0 or 1;
and pharmaceutically acceptable salts thereof, and individual enantiomers and diastereomers thereof.

2. The compound of claim 1 wherein Y is hydrogen.

3. The compound of any of claims 1-2 wherein $R^4$ is —$(CH_2)_s$-$Q^2$—$(CH_2)_t$, wherein $Q^2$ is selected from the group consisting of
(1) —O—, wherein s and t are 1, and
(2) —O—C(=O)—, wherein s is 1 and t is 0.

4. The compound of claim 1 wherein A is —$CH_3$.

5. The compound of claim 1 wherein $R^2$ is ($R^5$—$SO_2$)N($R^6$)—, wherein $R^5$ is methyl and $R^6$ is —$C_{1-6}$ alkyl.

6. The compound of claim 1 wherein the dotted line leading to $Q^3$ is absent, and $Q^3$ is $NR^x$, $R^x$ is hydrogen, and n is 1.

7. The compound of claim 1, wherein the dotted line leading to $R^y$ is absent and $R^y$ is selected from the group consisting of hydrogen and —$CH_3$.

8. A pharmaceutical composition comprising a therapeutically effective amount of a compound of claim 1 and a pharmaceutically acceptable carrier.

9. A method for inhibition of β-secretase activity in a mammal in need thereof which comprises administering to the mammal a therapeutically effective amount of a compound of claim 1.

10. The compound, or an individual enantiomer and/or diastereomer thereof, or a pharmaceutically acceptable salt of said compound or said individual enantiomer and/or diastereomer, said compound having a structure selected from the group consisting of:

| Structure |
| --- |
| 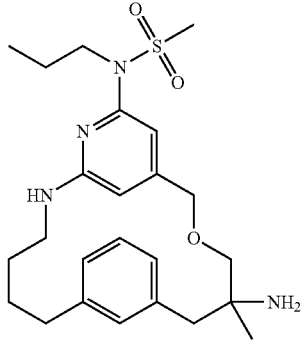 |
| 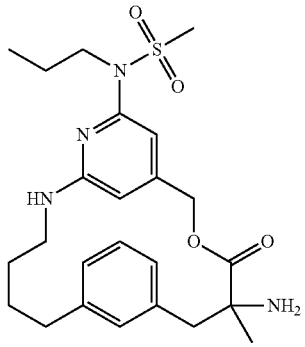 |

| 61 -continued | 62 -continued |
|---|---|
| Structure | Structure |
| 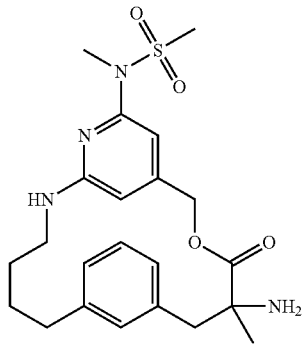 | 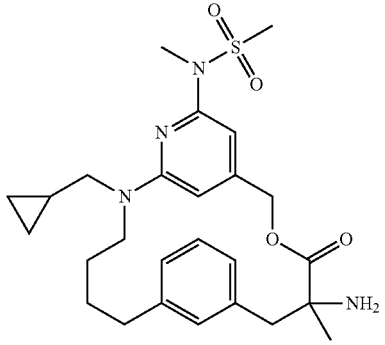 |
| 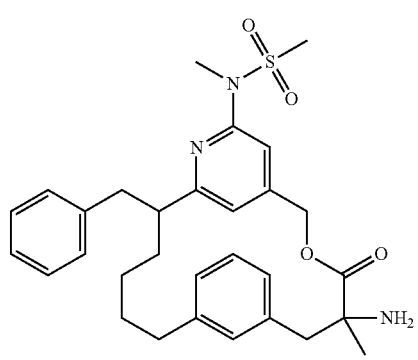 | 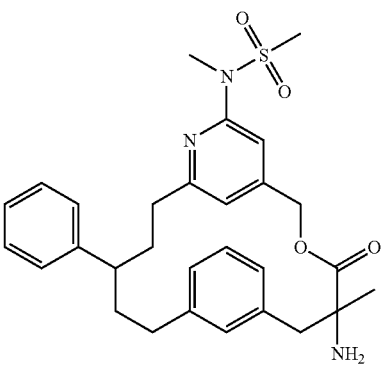 |
| 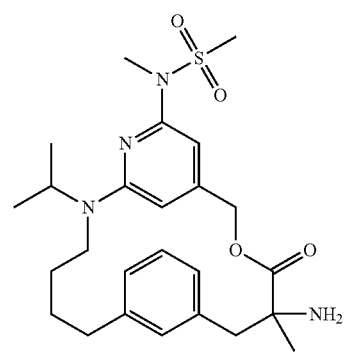 | 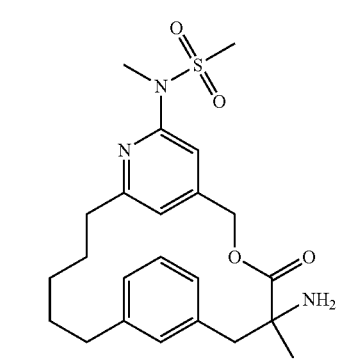 |
| 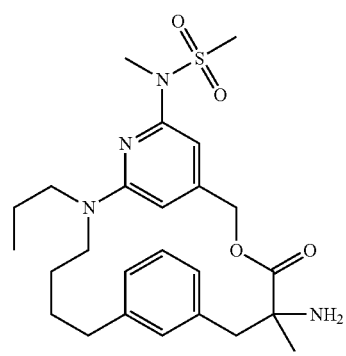 | 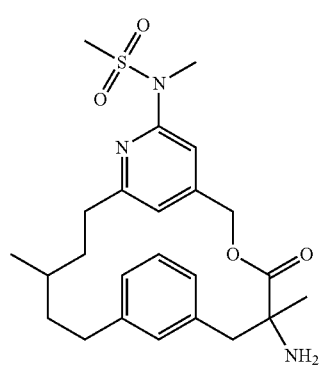 |

| Structure | | Structure |
|---|---|---|
| 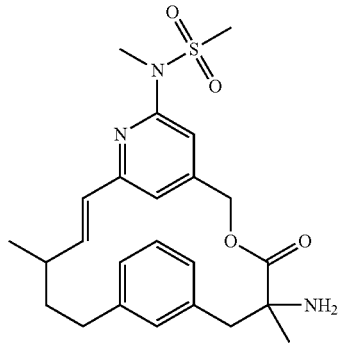 | | 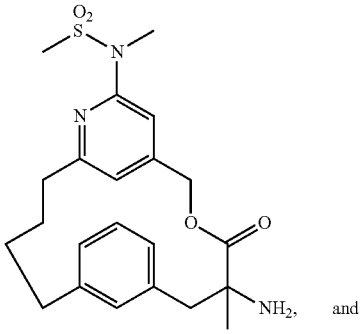 and |
| 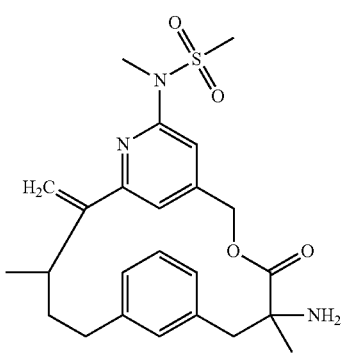 | | 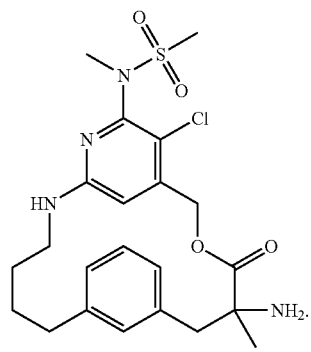 |
| 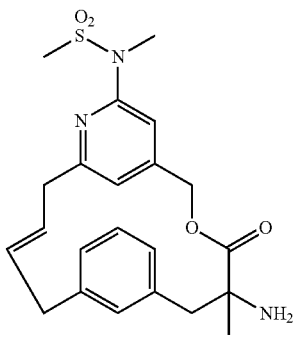 | | |
11. A pharmaceutical composition comprising a therapeutically effective amount of a compound of claim 10 and a pharmaceutically acceptable carrier.
12. A method for inhibition of β-secretase activity in a mammal in need thereof which comprises administering to the mammal a therapeutically effective amount of a compound of claim 10.
\* \* \* \* \*